United States Patent
Westpheling et al.

(10) Patent No.: US 12,325,859 B2
(45) Date of Patent: Jun. 10, 2025

(54) MICROBIAL APPROACH FOR THE PRODUCTION OF LONG CHAIN COMPOUNDS

(71) Applicants: UNIVERSITY OF GEORGIA RESEARCH FOUNDATION, INC., Athens, GA (US); UT-BATTELLE, LLC, Oak Ridge, TN (US); THE UNIVERSITY OF TENNESSEE RESEARCH FOUNDATION, Knoxville, TN (US)

(72) Inventors: Janet Westpheling, Bogart, GA (US); Adam M. Guss, Knoxville, TN (US); Lauren A. Riley, Lakewood, CO (US)

(73) Assignees: UT-Battelle, LLC, Oak Ridge, TN (US); University of Georgia Research Foundation, Inc, Athens, GA (US); University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 17/884,269

(22) Filed: Aug. 9, 2022

(65) Prior Publication Data

US 2023/0056452 A1 Feb. 23, 2023

Related U.S. Application Data

(60) Provisional application No. 63/230,906, filed on Aug. 9, 2021.

(51) Int. Cl.
*C12N 15/52* (2006.01)
*C12N 9/02* (2006.01)
*C12N 9/10* (2006.01)
*C12N 9/88* (2006.01)

(52) U.S. Cl.
CPC .......... *C12N 15/52* (2013.01); *C12N 9/0008* (2013.01); *C12N 9/1033* (2013.01); *C12N 9/88* (2013.01)

(58) Field of Classification Search
CPC .... C12N 15/52; C12N 9/0008; C12N 9/1033; C12N 9/88; C12N 9/16; C12N 9/13; Y02E 50/10; C12P 7/52; C12Y 301/02006; C12Y 402/01054; C12Y 208/03001; C12Y 401/01023; C12R 2001/01
See application file for complete search history.

(56) References Cited

U.S. PATENT DOCUMENTS 11,466,296 B2  10/2022  Guss et al.
2021/0024965 A1  1/2021  Guss et al.

FOREIGN PATENT DOCUMENTS

WO  WO 2023/018718 A1  2/2023

OTHER PUBLICATIONS

International Patent Application No. PCT/US2022/039833, filed Aug. 9, 2022; International Search Report and Written Opinion mailed Jan. 10, 2023; 19 pages.
American Type Culture Collection, Product Sheet for ATTC No. 25940, "Megasphaera elsdenii (Gutierrez et al.) Rogosa," Megasphaera elsdenii strain BE2-2083 [online]; Manassas, VA [retrieved on Feb. 16, 2024] from the Internet. Retrieved from the Internet:<URL: atcc.org/products/25940#detailed-product-information>; 6 pgs.
Choi et al., Metabolic engineering of microorganisms for the production of higher alcohols. mBio 5, e01524-01514 (2014).
Clomburg et al., A synthetic biology approach to engineer a functional reversal of the beta-oxidation cycle. *ACS Synth Biol* 1, 541-554 (2012).
De Rossi et al., Structural organization of pBC1, a cryptic plasmid from Bacillus coagulans. *J Bacteriol* 174, 638-642 (1992).
Dekishima et al., Extending carbon chain length of 1-butanol pathway for 1-hexanol synthesis from glucose by engineered *Escherichia coli*. *J Am Chem Soc* 133, 11399-11401 (2011).
Dellomonaco et al., Engineered reversal of the beta-oxidation cycle for the synthesis of fuels and chemicals. *Nature* 476, 355-359 (2011).
Elmore et al., Development of a high efficiency integration system and promoter library for rapid modification of Pseudomonas putida KT2440. Metab Eng Commun 5, 1-8 (2017).
Elmore et al., The SAGE genetic toolkit enables highly efficient, iterative site-specific genome engineering in bacteria. Posted Jun. 28, 2020; Retrieved from the Internet: <doi.org/10.1101/2020.06.28.176339> 19 pages.
Hatmaker et al., Complete Genome Sequences of Two Megasphaera elsdenii Strains, NCIMB 702410 and ATCC 25940. *Microbiol Resour Announc* 8, (2019).
Heap et al., A modular system for Clostridium shuttle plasmids. J Microbiol Methods 78, 79-85 (2009).
Kataoka et al., Butyrate production under aerobic growth conditions by engineered *Escherichia coli*. *J Biosci Bioeng* 123, 562-568 (2017).

(Continued)

*Primary Examiner* — Iqbal H Chowdhury
(74) *Attorney, Agent, or Firm* — Edna I. Gergel

(57) ABSTRACT

This disclosure describes recombinant *Megasphaera* microbes designed to include increased consumption of acetate, increased carbon flux to butyryl-CoA and/or hexanoyl-CoA, increased production of butyrate and/or hexanoate, or a combination thereof, than a comparable control. This disclosure also describes methods that generally include growing such recombinant microbes under conditions effective for the recombinant microbes to consume greater amounts of acetate, produce increased amounts of butyryl-CoA and/or hexanoyl-CoA, produce increased amounts of butyrate and/or hexanoate, or a combination thereof.

24 Claims, 8 Drawing Sheets

Specification includes a Sequence Listing.

(56) References Cited

OTHER PUBLICATIONS

Kim et al., Synthesis of medium-chain length (C6-C10) fuels and chemicals via beta-oxidation reversal in *Escherichia coli*. *J Ind Microbiol Biotechnol* 42, 465-475 (2015).
Lamsen et al., Recent progress in synthetic biology for microbial production of C3-C10 alcohols. *Front Microbiol* 3, 196 (2012).
Lipscomb et al., A Highly Thermostable Kanamycin Resistance Marker Expands the Tool Kit for Genetic Manipulation of Caldicellulosiruptor bescii. Appl Environ Microbiol 82, 4421-4428 (2016).
Liu et al., Establishment of a tractable genetic transformation system in *Veillonella* spp. *Appl Environ Microbiol* 78, 3488-3491 (2012).
Nelson et al., Mixed Carboxylic Acid Production by Megasphaera elsdenii from Glucose and Lignocellulosic Hydrolysate. *Fermentation* 3(10) (Mar. 2017).
Prabhu et al., Lactate and acrylate metabolism by Megasphaera elsdenii under batch and steady-state conditions. *Appl Environ Microbiol* 78, 8564-8570 (2012).
Projan et al., Replication properties of pIM13, a naturally occurring plasmid found in Bacillus subtilis, and of its close relative pE5, a plasmid native to *Staphylococcus aureus*. *J Bacteriol* 169, 5131-5139 (1987).
Riley et al., Approaches to genetic tool development for rapid domestication of non-model microorganisms. Biotechnol Biofuels 14, 30 (2021).
Singh et al., The complex mechanism of antimycobacterial action of 5-fluorouracil. *Chem Biol* 22, 63-75 (2015).
Tian et al., Simultaneous achievement of high ethanol yield and titer in Clostridium thermocellum. Biotechnol Biofuels 9, 116 (2016).
Tracy et al., Clostridia: the importance of their exceptional substrate and metabolite diversity for biofuel and biorefinery applications. *Curr Opin Biotechnol* 23, 364-381 (2012).
Weimer et al., Production of medium-chain volatile fatty acids by mixed ruminal microorganisms is enhanced by ethanol in co-culture with Clostridium kluyveri. *Bioresour Technol* 175, 97-101 (2015).
Zhang et al., Screening, expression, purification and characterization of CoA-transferases for lactoyl-CoA generation. *J Ind Microbiol Biotechnol* 46, 899-909 (2019).

SEQUENCE LISTING

```
Sequence total quantity: 29
SEQ ID NO: 1                moltype = DNA   length = 26
FEATURE                     Location/Qualifiers
source                      1..26
                            mol_type = other DNA
                            organism = synthetic construct
SEQUENCE: 1
tacgtctatc ggctttgtca gcagcg                                              26

SEQ ID NO: 2                moltype = DNA   length = 22
FEATURE                     Location/Qualifiers
source                      1..22
                            mol_type = other DNA
                            organism = synthetic construct
SEQUENCE: 2
ttttcaagcc gccagccgtg aa                                                  22

SEQ ID NO: 3                moltype = DNA   length = 25
FEATURE                     Location/Qualifiers
source                      1..25
                            mol_type = other DNA
                            organism = synthetic construct
SEQUENCE: 3
tcaaaggcct ccgcaatacg atcat                                               25

SEQ ID NO: 4                moltype = DNA   length = 25
FEATURE                     Location/Qualifiers
source                      1..25
                            mol_type = other DNA
                            organism = synthetic construct
SEQUENCE: 4
acatcgtcca cttcgaaggc gatgt                                               25

SEQ ID NO: 5                moltype = DNA   length = 23
FEATURE                     Location/Qualifiers
source                      1..23
                            mol_type = other DNA
                            organism = synthetic construct
SEQUENCE: 5
gaacttgaat tgccaaagga agt                                                 23

SEQ ID NO: 6                moltype = DNA   length = 27
FEATURE                     Location/Qualifiers
source                      1..27
                            mol_type = other DNA
                            organism = synthetic construct
SEQUENCE: 6
gtaagctagc tcagatcctt ccgtatt                                             27

SEQ ID NO: 7                moltype = DNA   length = 26
FEATURE                     Location/Qualifiers
source                      1..26
                            mol_type = other DNA
                            organism = synthetic construct
SEQUENCE: 7
aggtgtccat gcaggtaaac ctcctt                                              26

SEQ ID NO: 8                moltype = DNA   length = 25
FEATURE                     Location/Qualifiers
source                      1..25
                            mol_type = other DNA
                            organism = synthetic construct
SEQUENCE: 8
gtttacctgc atggacacct acgcg                                               25

SEQ ID NO: 9                moltype = DNA   length = 24
FEATURE                     Location/Qualifiers
source                      1..24
                            mol_type = other DNA
                            organism = synthetic construct
SEQUENCE: 9
aaggatctga gctagcttac gccg                                                24

SEQ ID NO: 10               moltype = DNA   length = 51
FEATURE                     Location/Qualifiers
source                      1..51
                            mol_type = other DNA
                            organism = synthetic construct
```

-continued

```
SEQUENCE: 10
cgcctttgag tgagctgata ccgcacatcc aagtctataa tacgccgcag c         51

SEQ ID NO: 11          moltype = DNA   length = 45
FEATURE                Location/Qualifiers
source                 1..45
                       mol_type = other DNA
                       organism = synthetic construct
SEQUENCE: 11
catgctccaa cagcaaaaag gaaaattagt actcggcgcc gatca                45

SEQ ID NO: 12          moltype = DNA   length = 22
FEATURE                Location/Qualifiers
source                 1..22
                       mol_type = other DNA
                       organism = synthetic construct
SEQUENCE: 12
tcctttttgc tgttggagca tg                                         22

SEQ ID NO: 13          moltype = DNA   length = 23
FEATURE                Location/Qualifiers
source                 1..23
                       mol_type = other DNA
                       organism = synthetic construct
SEQUENCE: 13
gcggtatcag ctcactcaaa ggc                                        23

SEQ ID NO: 14          moltype = DNA   length = 28
FEATURE                Location/Qualifiers
source                 1..28
                       mol_type = other DNA
                       organism = synthetic construct
SEQUENCE: 14
gatttcacac taatcgttca tcgacgta                                   28

SEQ ID NO: 15          moltype = DNA   length = 30
FEATURE                Location/Qualifiers
source                 1..30
                       mol_type = other DNA
                       organism = synthetic construct
SEQUENCE: 15
tgaacgatta gtgtgaaatc tcctttccta                                 30

SEQ ID NO: 16          moltype = DNA   length = 35
FEATURE                Location/Qualifiers
source                 1..35
                       mol_type = other DNA
                       organism = synthetic construct
SEQUENCE: 16
aagcctggtt gcatgcttca ggtttgtctg taact                           35

SEQ ID NO: 17          moltype = DNA   length = 34
FEATURE                Location/Qualifiers
source                 1..34
                       mol_type = other DNA
                       organism = synthetic construct
SEQUENCE: 17
tacttgtacg tgcatctaag ttccctctca aatt                            34

SEQ ID NO: 18          moltype = DNA   length = 33
FEATURE                Location/Qualifiers
source                 1..33
                       mol_type = other DNA
                       organism = synthetic construct
SEQUENCE: 18
tgagagggaa cttagatgca cgtacaagta atg                             33

SEQ ID NO: 19          moltype = DNA   length = 29
FEATURE                Location/Qualifiers
source                 1..29
                       mol_type = other DNA
                       organism = synthetic construct
SEQUENCE: 19
tcagggagat ggcccttatt tcgtgccga                                  29

SEQ ID NO: 20          moltype = DNA   length = 27
FEATURE                Location/Qualifiers
source                 1..27
                       mol_type = other DNA
```

-continued

```
                      organism = synthetic construct
SEQUENCE: 20
ttcggcacga aataagggcc atctccc                                              27

SEQ ID NO: 21         moltype = DNA  length = 29
FEATURE               Location/Qualifiers
source                1..29
                      mol_type = other DNA
                      organism = synthetic construct
SEQUENCE: 21
cagacaaacc tgaagcatgc aaccaggct                                            29

SEQ ID NO: 22         moltype = DNA  length = 1554
FEATURE               Location/Qualifiers
source                1..1554
                      mol_type = genomic DNA
                      organism = Megasphaera elsdenii
SEQUENCE: 22
atgagaaaag tagaaatcat tacagctgaa caagcagctc agctcgtaaa agacaacgac    60
acgattacgt ctatcggctt tgtcagcagc gccatccgg aagcactgac caaagctttg    120
gaaaacggt tcctggacac gaacacccg cagaacttga cctacatcta tgcaggctct    180
cagggcaaac gcgatggccg tgccgctgaa catctgcaac acaggcct tttgaaacgc    240
gccatcatcg gtcactggca gactgtaccg gctatcggta aactggctgt cgaaaacaag    300
attgaagctt acaacttctc gcagggcacg ttggtccact ggttccgcgc cttggcaggt    360
cataagctcg gcgtcttcac cgacatcggt ctggaaactt cctcgatcc ccgtcagctc    420
ggcggcaagc tcaatgacgt aaccaaagaa gacctcgtca aactgatcga agtcgatgt    480
catgaacagc ttttctaccc gaccttcccg gtcaacgtag cttcctccg cggtacgtat    540
gctgatgaat ccggcaatat caccatggac gaagaaatcg ggcctttcga aagcacttcc    600
gtagcccagg ccgttcacaa ctgtggcggt aaagtcgtcg tccaggtcaa agacgtcgtc    660
gctcacggca gcctcgaccc gcgcatggtc aagatcctat cgatctatgt cgactacgtc    720
gtcgtagcag ctccggaaga ccatcagcag acgtatgact gcgaatacga tccgtccctc    780
agcggtgaac atcgtgctcc tgaaggcgct accgatgcag ctctccccat gagcgctaag    840
aaaatcatcg gccgccgcgg cgctttggaa ttgactgaaa acgctgtcgt caacctcggc    900
gtcggtgctc cggaatacgt tgcttctgtt gccggtgaag aaggtatcgc cgataccatt    960
accctgaccg tcgaaggtgg cgccatcggt ggcgtaccgc agggcggtgc ccgcttcggt    1020
tcgtcccgca atgccgatgc catcatcgac cacacctatc agttcgactt ctacgatggc    1080
ggcggtctgg acatcgctta cctcggcctg cccagtgcg atggctcggg caacatcaac    1140
gtcagcaagt tcggtactaa cgttgccggc tgcggcggtt tcccaacat ttcccagcag    1200
acaccgaatg tttacttctg cggcaccttc acggctggcg gcttgaaaat cgctgtcgaa    1260
gacggcaaag tcaagatcct ccaggaaggc aaagcaaga agttcatcaa agctgtcgac    1320
cagatcactt tcaacggttc ctatgcagcc cgcaacggca aacacgttct ctacatcaca    1380
gaacgctgcg tatttgaact gaccaaagaa ggcttgaaac tcatcgaagt cgcaccgggc    1440
atcgatattg aaaagatat cctcgctcac atggacttca agccgatcat tgataatccg    1500
aaactcatgg atgcccgcct cttccaggac ggtcccatgg gactgaaaaa ataa          1554

SEQ ID NO: 23         moltype = DNA  length = 1584
FEATURE               Location/Qualifiers
source                1..1584
                      mol_type = genomic DNA
                      organism = Megasphaera elsdenii
SEQUENCE: 23
atgaagcaag tgaaaataat tacagcgcaa gaagcagcac agctcgtcaa agacggtgac    60
gtcgttacga ctaacgggtt cgtcggttcc ggccagccgg aagccttgac cagtgccctg    120
gaagaacgct tcctcaacac gggttcgccg aaagatttga ccctcatcta tgccgcttcc    180
caagggaata cggacggccg cggcggcgac cacttcgaca acgaagggat gctgaaaaaa    240
gccatcctcg gccattgaa tgctgttact tctttacaga aattagtcaa tgaaaataaa    300
atccaggctt ataacctgcc gcagggcacg ttgtccccagt acttccgcga cgtcgcagct    360
catcgcttag gcacgattac ccacgtcggc ctcgatacct ttgccgaccc ccgcatcagc    420
ggcggccgcc tcaatgacgt caccaaagaa gattttgtca aagtcatcaa catcgaaggc    480
catgaccagc tcttctatcc gcgcatggat atgaatatcg gcttcatccg cgggacttat    540
gccgatgaat ggggcaacgt cgttatgagc aaggaagtat cgccttttga tgctacaccg    600
ctggcacagg ccgtccataa cagcggcggt atcgtcgtcg tccaggtcga aaaatcgtc    660
aaaggcggca cgctcgaccc gaaactggtc aaagtaccgg gcatctatgt cgactatatc    720
gtccaggtcg atgatgaaac gaaacggcag cagtccttga ttgcgaata cgatccgtcc    780
ctgaccggg aaacgacgat tcctgtcaaa gccctcgatc cggctccgct caatgccaag    840
aaagtcattg cccgccggc agctctcctg ctcctcaata tgagcaatga agccgtcatc    900
aacctgggta tcgtattccc ggaactcgtt tcgtcggttg ctaacgaaga aggcatcggc    960
gacagcctga ccatgactgt cgaagccggg gctatcggcg gcgttcccct cggcggcgtc    1020
cgcttcggtg cttctgtcaa tgccgaagct tatatgacc aggctaccca gttcgacttc    1080
tacgatggcg gcggtctgga cctgacctgc ctgggcctgg ctgaatgtga taagacggc    1140
aacatcaacg tatccaaatt cggtacgcgt atcgctggct gcggcggctt cgtcaacatc    1200
acccagaata cgaagaacgt cgtcttctgc ggcaccttca cgacaggaa actccgcgaa    1260
gaaatcaaag atggcgaact gcacatcacg caggaaggga aagtcaagaa attcgtcccc    1320
gaagtcgaca acattacctt cagcggcaac tatgcccgga acataaaca gcatgtcctc    1380
tacattacgg aacgtgccgt attcgaaatg aaggaagatg cgtccatct gacagaaatc    1440
gcaccggcg tcgacctcca gaaagatgtc ctcgaccaga tgggcttcaa accgatcatc    1500
gacgacgtca aactcatgcc ggccttcctc ttcgaagata aacccatggg cctgaaaaag    1560
atgaaagaag aaatgaataa ataa                                              1584
```

| SEQ ID NO: 24 | moltype = DNA  length = 1557 |
|---|---|
| FEATURE | Location/Qualifiers |
| source | 1..1557 |
| | mol_type = genomic DNA |
| | organism = Megasphaera elsdenii |

SEQUENCE: 24

| | | | | | | |
|---|---|---|---|---|---|---|
| atgacacagt | ttattacgcc | ggccgaagcg | gcgcgtctcg | tcggcgatga | tatgaccctg | 60 |
| gctgtcagcg | gtcatgccgg | cttcggtacg | cctgatggtt | tattcaaggc | tctccacgac | 120 |
| cgctatgccg | acgaagggca | tccccgcaac | gtgaccttgg | tcaagattgc | cggtactggc | 180 |
| gacggggcc | agcgcggcgg | tgaccgactg | gctgcagacg | gcctcattgg | gacaatcatt | 240 |
| accagtcatt | ttggcatgga | aaagaaatta | tccgataagg | tcgcagctga | ccagtgcctg | 300 |
| gcctatacgt | tcccggctgg | gacgctcctg | gaactgtacc | gggctattgc | cgccggccgt | 360 |
| aagggcgtct | ggaccgacat | cggcctgcat | accctggccg | acccgcgccg | ggacggcagc | 420 |
| aaggccaatg | aaaagaccgt | ccgcgaaggg | aaagacatcg | tccgcttgat | ggaaatcgat | 480 |
| ggcagcgaat | acctgtatta | tccggccttt | cccatccagg | tctgcttcat | ccgcggctcc | 540 |
| ctggccgatg | aagacggcaa | catttccctc | cagcgcgaag | ccatgatcgg | tgaacagctg | 600 |
| gaagtggccg | aagcgacgca | taattccggc | ggcatcgtcg | tcgtccaggt | cgaagacgtc | 660 |
| gtgccccggg | gaagcctcga | ttcgcccctc | gtgaagattc | accattttcct | cgtcgactac | 720 |
| gtcgtcgtac | cgcggccgaa | gtatcacgtc | cagagctttt | cgaccccatgg | ctaccggccg | 780 |
| gaactgagcg | gcgaagggcg | caagtccatc | cagtccctgc | cgccccatcc | cctggacaac | 840 |
| cgcaagatct | gtgcccgccg | ggccgccatg | gaactgaaga | agggcgatgt | catgaacctg | 900 |
| ggaatcggta | tcccggaaat | catcggttct | gtcgccgccg | aagaaggctt | cggggccgagc | 960 |
| ttgaccctgg | ctgccgattc | gggcatcatc | ggtggcatcc | ccttgtcggg | cctcgatatg | 1020 |
| ggagcggctg | tcaatgccga | agccgagctg | aagatggccg | acatgttcga | catctgccac | 1080 |
| ggcggcggcc | tcgacctctg | cgccctgggc | ctggcggaaa | tcgacgccat | gggcaatgtc | 1140 |
| aatgtctcga | aattccacgg | ccgcgtcacc | ggaccaggag | gcttcatcga | tctggcccag | 1200 |
| cctacgaaga | aactcatcct | catggggacc | tttacggccg | gcggcctgcg | ggaacactgc | 1260 |
| gaagacgggc | gcctggtcat | cgaccatgaa | gggaaatacc | agaagttcaa | gacggacatc | 1320 |
| gaacaggtca | cttttttccgg | gtcttatgcg | gccagtcatg | accagcacgt | cctggtcgtc | 1380 |
| actgaacggg | ccgtcttccg | cctgacacag | cagggcctga | tgctgacgga | aatcgcccg | 1440 |
| ggcatggacc | tggaacggga | catcctggga | cagatggaat | ttcgcccgct | catcgccgac | 1500 |
| gacctgcgac | tcatggacag | ccgcatcttc | cagcccaatc | ccatggggat | aacgtaa | 1557 |

| SEQ ID NO: 25 | moltype = DNA  length = 1551 |
|---|---|
| FEATURE | Location/Qualifiers |
| source | 1..1551 |
| | mol_type = genomic DNA |
| | organism = Megasphaera elsdenii |

SEQUENCE: 25

| | | | | | | |
|---|---|---|---|---|---|---|
| atggcaaaac | tgattacagc | agaaaatgca | gcatcgctta | ttaagaatcg | ttcgactatc | 60 |
| gccgtttgtg | gttttgcaca | gtgtgcatta | ccggaagaag | tattgcaggc | cctgaaagac | 120 |
| cgcttttacca | agaccggata | tccgcagcag | ctgacactgg | tccatacagc | cggcatcggt | 180 |
| gacggtgtga | gcaaaggtgc | cagccatttc | gcccatgaag | gcatgctgaa | acgggtcatt | 240 |
| gccggtcatt | ataacctggc | tcccaaactg | ggtaaattgg | tcatggacaa | caaggtcgaa | 300 |
| ggctataacc | tgccgcaggg | tacgatggct | cagtggttcc | gcagcattgc | cggccgcaag | 360 |
| ccgggcctct | tcacccgcgt | cggcctcaat | acgttcgtcg | accccgcat | tgaaggcggt | 420 |
| aaattgaaca | gcatcaccaa | ggaagacctg | gtagaagtga | aggaattgga | tggtgaagaa | 480 |
| tacttgtggt | acaaaccgtt | ccccattgac | gtcgctatcg | tccacgggac | ttgtgccgac | 540 |
| ttgaacggta | acgtatcgac | ggataacgaa | gaagtccgca | tggagctcct | gcccatggcc | 600 |
| ctggcagcca | agccagcgg | cggcatggtc | atcgtccagg | tcgaaacgtt | ggccgaaaac | 660 |
| cggacgattc | cgccgaaaca | cgtcgtcctc | ccgggcacga | acgtcgacta | catcgtcttg | 720 |
| tccaaggtcc | gtcaggtcca | gaaccccggc | tataccggtg | aaatgcgtat | gcctctgtcc | 780 |
| cagattccgc | cgatggcact | caacgcccgt | aagtcattg | cccgccgggc | tgcgatggaa | 840 |
| ctcgtaccca | acgccgtcgt | caacttgggc | atcgggattc | cggaaggcgt | ctccagtgta | 900 |
| gccaatgaag | aaggtatcgg | cgatcagctg | acactgactg | tcaagccgga | accgattgcc | 960 |
| ggtgtaccgg | ccagcggcgc | tgactttggc | ggatcggcca | acgccgatgc | aatcgtcgac | 1020 |
| catccgtatc | agttcgactt | ttacgatggc | ggcgggctgg | acatggcttt | cctgggcatg | 1080 |
| gctgaatgta | acgccaaagg | cgatgtcaat | gtcagtaagt | tcaaagaccg | catcgccggc | 1140 |
| tgtggcggtt | tcatcaacat | cacccagaac | acgcataaag | tcgtcttctg | cggtaccttc | 1200 |
| acggctaaag | gcctgcgcga | agaaatccgc | gacggcaaag | tggtcatcat | ccatgaaggg | 1260 |
| gctgtccaga | aattcatcga | taaggtcggc | cagattactt | tcagtgctga | ctatgctcac | 1320 |
| aaacataatc | agcaggtcat | gttcattacc | gaacgctgcg | tcttcgtcct | caccgacaaa | 1380 |
| ggcctggtcc | tcacggaaat | cgcaccgggc | gtggatctgc | aaaaggatat | cctcgaccag | 1440 |
| atggaattcg | tgccgcacat | tgccgaagac | ctgaagacca | tggacgaacg | aatcttccgc | 1500 |
| gatgaaccca | tgggcctggc | gcaggacatc | tttgaacagc | aagccagcta | g | 1551 |

| SEQ ID NO: 26 | moltype = DNA  length = 738 |
|---|---|
| FEATURE | Location/Qualifiers |
| source | 1..738 |
| | mol_type = genomic DNA |
| | organism = Megasphaera elsdenii |

SEQUENCE: 26

| | | | | | | |
|---|---|---|---|---|---|---|
| gtgttatcga | aggtatttc | tctccaagat | atcctggagc | atatccatga | cggacagacc | 60 |
| atcatgttcg | gtgactgtca | tggccaattc | gccggctgatg | aaatcatcga | cggcatgctg | 120 |
| gaaaaaggcg | tcaaggatat | caaagccatc | gccgtatcgg | ccggctatcc | cggccagggc | 180 |
| gtaggcaagc | tgatcgtggc | tcatcgcgtg | tcgtccatcg | ttacgacgca | tatcggcctc | 240 |
| aatccggaag | cgctgaaaca | gatgctggcc | ggtgaactgg | ccgtcgaatt | cgtccccag | 300 |
| gggacctggg | ccgaacgcgt | gcgctgcggc | ggtgccggcc | tgggcggcgt | cctgacgccg | 360 |
| accggtgtcg | gtacgagtgt | cgaagaaggg | aaacagaagc | tggtcatcga | tgggaaggaa | 420 |

```
tatctcctgg aattaccgct ccatgccgac gtagccctgg tcaaggcgac caaagccgat   480
acggcaggga acctctattt ccgcatgaat tcgcgggcga cgaacagtac catcgcttat   540
gcggctgatt tcgtcgccgc cgaagtcgaa gaaatcgtcc ccgtcggcca gctcttgccg   600
gaagaaatcg ccatcccggc tcctgtcgtc gacatggtct atgaacggca gggcgaaaaa   660
cggtttatct gcccgatgtg gaaaaaggcc agggcccgtg ccgaagccaa ggcgcgggaa   720
cggcaggaaa ggggatga                                                 738

SEQ ID NO: 27           moltype = DNA   length = 915
FEATURE                 Location/Qualifiers
source                  1..915
                        mol_type = genomic DNA
                        organism = Megasphaera elsdenii
SEQUENCE: 27
atgaaaccaa tgagactaca tcacgtaggc attgtcctgc cgaccttaga aaaagcccat   60
gaattcatgc agaataatgg acttgaaatc gactatgccg gctatgtcga tgcttaccag   120
gctgatctca ttttcactaa gtttggtgaa tttgccagcc cgattgaaat gattatcccg   180
cactccggtg tgcttaccca attcaatggt ggccgcggcg gcattgccca tcgccttc    240
gaagtggacg atgtcgaagc tgtccgccag gaaatggaag cagattgtcc gggatgcatg   300
ttagaaaaga aagctgtcca gggtacggac gacattatcg tcaacttccg ccgcccgaca   360
accaaccagg gtatcctcgt tgaatatgtt cagacgacag cacctatcac cggccgcggc   420
gaaaatcctt tcgttaagaa tctcggcccg gaaaagggga agctcaacga acatggcat    480
cccatgcgcc tgcaccatat cggcatcgtc ttgccgacct tggaaaaggc ccatgaattc   540
atcaagacca atggtctgga agtggattat tccggtttcg tcgacgccta ccatgcggat   600
ctcatttttca ctaaaaaagg tgaaaacagt acgccatcg aattcattat tccccgtgaa   660
ggggtcctca aagatttcaa tcatggcagg ggaggtatcg ctcatatcgc ctttgaagtg   720
gatgatgtcg aaaaggtacg tcagattatg gaaagccagt agctcggttg catgctcgga   780
aagaaagccg tccggggaac ggacgatatc atcgtcaact tccgccgtcc cagcacggac   840
gccggcatcc tcgtcgaata tgtccagacc gtagctccca tcaatcgcag caatcccaac   900
ccttttaatg attga                                                    915

SEQ ID NO: 28           moltype = DNA   length = 1287
FEATURE                 Location/Qualifiers
source                  1..1287
                        mol_type = genomic DNA
                        organism = Megasphaera elsdenii
SEQUENCE: 28
atgagtgaag aaaaaacagt agatattgaa agcatgagct ccaaggaagc ccttggttac   60
ttcttgccga aagtcgatga gacgcacgt aaagcgaaaa aagaaggccg cctcgtttgc   120
tggtccgctt ctgtcgctcc tccggaattc tgcacggcta tggacatgcc catcgtctta   180
ccggaaactc acgcagctgg tatcggtgcc cgtcacggtg ctccggccat gctcgaagtt   240
gctgaaaaca aaggttacaa ccaggacatc tgttcctact gccgcgtcaa catgggctac   300
atggaactcc tcaaacagca ggctctgaca ggcgaaacgc cggaagtcct caaaaactcc   360
ccggcttctc cgattcccct tccggatgtt gtcctcactt gcaacaacat ctgcaatacc   420
ttgctcaaat ggtatgaaaa cttggctaaa gaattgaacg tacctctcat caacatcgac   480
gtaccgttca accatgaatt ccctgttacg aaacacgcta acagtacat cgtcggcgaa   540
ttcaaacatg ctatcaaaca gctcgaagac ctttgcggcc gtcccttcga ctatgacaaa   600
ttcttcgaag tacagaaaca gacacagcgc tccatcgctg cctggaacaa aatcgctacg   660
tacttccagt acaaaccgtc gccgctcaac ggcttcgacc tcttcaacta catgggcctc   720
gccgttgctg cccgctcctt gaactactcg gaaatcacgt tcaacaaatt cctcaaagaa   780
ttggacgaaa aagtagctaa taagaaatgg ctttcggtg aaaacgaaaa atcccgtgtt   840
acttggggaa gtatcgctgt ctggatcgct tccggccaca ccttcaaaga actcaaaggt   900
cagggcgctc tcatgactgg ttccgcttat cctggcatgt gggacgtttc ctacgaaccg   960
ggcgacctcg aatccatggc agaagcttat tcccgtacat acatcaactg ctgcctcgaa   1020
cagcgcggtg ctgttcttga aaaagttgtc cgcgatggca aatgcgacgg cttgatcatg   1080
caccagaacc gttcctgcaa gaacatgagc ctcctcaacg gcaaaggcgg ccagcgcatc   1140
cagaagaacc tcggcgtacc gtacgtcatc ttcgacggcg accagaccgt tgctcgtaac   1200
ttctcggaag cacagttcga tacccgcgta gaagctttgg cagaaatgat ggcagacaaa   1260
aaagccaatg aaggaggaaa ccactaa                                       1287

SEQ ID NO: 29           moltype = DNA   length = 714
FEATURE                 Location/Qualifiers
source                  1..714
                        mol_type = genomic DNA
                        organism = Megasphaera elsdenii
SEQUENCE: 29
atggcagatg atcgcatcat tacggctttg gatgtccatt cactggagga tatgaagaag   60
ctcgtagaaa cccttggcga cagtgtttct ttttataaag tcggcatgga actgtttac    120
agtgccggtc ccgacgcagt acggtatttg aaggaccagg ggaaacatgt ttcctcgat    180
ttgaaggtcc atgatattcc caatacggta ggccagagca tccgcgccct gacccgtctc   240
ggcgccgacc tcatgacgct gcacggcaca ggtggccggg ccatgatgga agcggctgc    300
gaagccgtcc gcgatgaagc ggccaagctg aatatcgaac ggcctcgcct tttggctgtg   360
acggtattga ccagcatcga tgaagatgcg tggaaagaaa tcgcggcaa gtacagcatt   420
gccgaatcgg tcaagaacct ggctaaactg ccaaggaag ccggtatcga cgggaccgtt   480
tcttcgccgt atgaagcgaa ggaaatccgg gaaatgaatg gtcccgattt cctcatcgtc   540
acgccgggca tccggcgac ctttgccgta gccaacgacc agaagcggtt cacgacgccg   600
tcccaggctt tgcgcgacgg ggcatccat ttggtcatcg gtcgtccgat taccaaggct   660
gccgatccga aagaagcagc ggaaaagatt ttagcagaaa ttcaggggt ataa          714
```

MICROBIAL APPROACH FOR THE PRODUCTION OF LONG CHAIN COMPOUNDS

CROSS-REFERENCE TO RELATED APPLICATIONS

This application claims the benefit of U.S. Provisional Application Ser. No. 63/230,906, filed Aug. 9, 2021, which is incorporated by reference herein in its entirety.

GOVERNMENT FUNDING

This invention was made with government support under grant numbers DE-SC0019401 and DE-AC05-00OR22725 awarded by the DOE. The government has certain rights in the invention. (37 CFR 401.14 f (4)).

SEQUENCE LISTING

This application contains a Sequence Listing electronically submitted via EFS-Web to the United States Patent and Trademark Office as an XML file entitled "0235000295US01_UPDATE.xml" having a size of 36,610 bytes and created on Nov. 19, 2024. The information contained in the Sequence Listing is incorporated by reference herein.

BACKGROUND

Greenhouse gas emissions and the enormous carbon footprint of transportation have contributed to the impending climate crisis of the planet. The advancement of the biofuel industry to create carbon-neutral processes such as drop-in and replacement fuels for petroleum-based gasoline is critical in resolving the transportation industry's contribution to the climate crisis (Nelson 2017, Lamsen 2012). The current model for drop-in fuels is largely based on ethanol produced industrially from starches in corn feedstocks. Though this ethanol produced from starch has a positive energy balance and already contributes to lowered emissions when added to gasoline, farming practices, including land use, is a concern for corn-based bioethanol production and have the potential to be greatly lowered (afdc.energy.gov/fuels/ethanol_fuel_basics.html) (Tracy 2011). The development of next-generation biofuels such as longer chain-length alcohols like butanol and hexanol offers the opportunity for increasing the efficiency of the biofuels produced and reducing carbon-based fuel emissions (Choi, Lamsen 2021). Longer-chain alcohols and fatty acid production has been seen in a variety of organisms, including but not limited to many Clostridia (Choi, Tracy, Weimer). Heterologous chain-elongation pathways have been expressed in *E. coli*, but organisms with native flux condensing acetyl-coA groups are more robust in their ability to form the end-products, and, ultimately, engineering these pathways in *E. coli* was not seen to produce these alcohols in industrially relevant fluxes (Dekishima 2011, Clomburg 2012, Kataoaka 2017, Dollomonaco 2011, Kim 2015).

SUMMARY OF THE APPLICATION

*Megasphaera elsdenii* is a ruminal mesophilic obligate anaerobe that is a member of the Negativicutes class of bacteria that natively possesses high-flux energy metabolism from a variety of carbon sources to fatty acid pre-cursors of alcohols with longer chain-length than acetate, including butyric acid, hexanoic acid, and even octanoic acid (Nelson 2017, Prabhu 2012). These native metabolic abilities make *M. elsdenii* a uniquely promising organism for metabolic engineering and optimization of drop-in biofuel production of the longer-chain alcohol biofuels of the future. Additionally, this work takes full advantage of this novel organism that has already been used in fermentation studies (Nelson 2017, Prabhu 2012), but has not been genetically tractable to genetic engineering until recently. With advanced sequencing technologies, transcriptomics, and cross-phylogeny implementation of other rapid genetic tools now available, the abilities of *M. elsdenii* can be exploited to serve as a platform for the production on longer chain alcohols. These tools include the development of a strategy for the use of a counter-selectable marker in this work for targeted enzyme deletions to increase flux towards targeted products, utilizing the gene upp (uracil phosphoribosyltransferase), which allows for the use of counter-selection against an integrated vector using 5-fluorouracil, and the gene pyrF (orotidine-5'-phosphate decarboxylase), which allows for the use of counter-selection against an integrated vector using 5-fluoroorotic acid (5-FOA).

Relatively little is known about *Megasphaera elsdenii* metabolism and the biochemical activities of its chain elongation and organic acid production enzymes. Metabolic engineering efforts in this organism will be greatly bolstered by a better understanding of the roles of these enzymes in metabolism and its flux, and, as a result of the ambiguous nature of genome annotation, the functions of its putative organic acid production enzymes are unknown, including its various acyl-CoA transferases. As described herein, genetic links between putative chain elongation enzymes and organic acid fermentation products in *M. elsdenii* are identified using newly developed genetic tools to construct a chromosomal marker replacement of a putative propionyl-CoA transferase gene, locus tag: MELS_0742, and others. The resulting phenotype of this mutant strain is then observed to elucidate the resulting fermentation profile and growth phenotypes of this single mutant.

Terms used herein will be understood to take on their ordinary meaning in the relevant art unless specified otherwise. Several terms used herein and their meanings are set forth below.

As used herein, the terms "genetically engineered" microbe and "recombinant" microbe are used interchangeably and refer to a microbe that has been altered by human intervention. For example, a "recombinant" microbe refers to a microbe that has been genetically manipulated. In one or more embodiments, a recombinant microbe is one that includes alteration of endogenous nucleotides. For example, a microbe is a genetically modified microbe by virtue of introduction of an alteration of endogenous nucleotides. For instance, an endogenous coding region could be deleted or mutagenized. Another example of a recombinant microbe is one into which has been introduced an exogenous polynucleotide and expresses a protein from the exogenous polynucleotide. Yet another example of a genetically modified microbe is one having an altered regulatory sequence, such as a promoter, to result in increased or decreased expression of an operably linked endogenous coding region.

As used herein, an "exogenous polynucleotide" refers to a polynucleotide that is not normally or naturally found in a microbe. An exogenous polynucleotide includes a coding region that is not normally found in a microbe, and a coding region that is normally found in a microbe but is operably linked to a regulatory region to which it is not normally linked. An "endogenous polynucleotide" is also referred to as a "native polynucleotide."

As used herein, the term "protein" refers broadly to a polymer of two or more amino acids joined together by peptide bonds. The term "protein" also includes molecules which contain more than one protein joined by a disulfide bond, or complexes of proteins that are joined together, covalently or noncovalently, as multimers (e.g., dimers, tetramers). Thus, the terms peptide, oligopeptide, enzyme, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region," "coding sequence," and "CDS," are used interchangeably and refer to a nucleotide sequence that encodes a protein and, when placed under the control of appropriate regulatory sequences expresses the encoded protein. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

Genetic loci of a *Megasphaera*, such as an *M. elsdenii*, are referred to herein using one of two locus tag identifiers. One locus tag identifier has the prefix "MELS_" followed by the number of the CDS in the *Megasphaera elsdenii* strain DSM 20460 draft genome, GenBank accession HE576794.1. The second locus tag identifier has the prefix "MELS_RS" followed by the number of the CDS in the *Megasphaera elsdenii* strain DSM 20460 complete sequence, GenBank accession NC 015873.1. Genetic loci described herein include MELS 0742 (SEQ ID NO: 22), MELS 0464 (SEQ ID NO:23), MELS 1631 (SEQ ID NO: 24), MELS 1130 (SEQ ID NO: 25), MELS 0034 (SEQ ID NO: 26), MELS 0743 (SEQ ID NO: 27), MELS 0745 (SEQ ID NO: 28), MELS RS4415 (SEQ ID NO: 29).

Unless otherwise specified, "a," "an," "the," and "at least one" are used interchangeably and mean one or more than one.

As used in this specification and the appended claims, the term "or" is generally employed in its sense including "and/or" unless the content clearly dictates otherwise. The term "and/or" means one or all of the listed elements or a combination of any two or more of the listed elements. The use of "and/or" in some instances does not imply that the use of "or" in other instances may not mean "and/or."

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "have," "has," "having," "include," "includes," "including," "comprise," "comprises," "comprising" or the like are used in their open ended inclusive sense, and generally mean "include, but not limited to," "includes, but not limited to," or "including, but not limited to."

It is understood that wherever embodiments are described herein with the language "have," "has," "having," "include," "includes," "including," "comprise," "comprises," "comprising" and the like, otherwise analogous embodiments described in terms of "consisting of" and/or "consisting essentially of" are also provided. The term "consisting of" means including, and limited to, whatever follows the phrase "consisting of." That is, "consisting of" indicates that the listed elements are required or mandatory, and that no other elements may be present. The term "consisting essentially of" indicates that any elements listed after the phrase are included, and that other elements than those listed may be included provided that those elements do not interfere with or contribute to the activity or action specified in the disclosure for the listed elements.

Conditions that are "suitable" for an event to occur, such as replication of a microbe or positive selection of a marker, or "suitable" conditions are conditions that do not prevent such events from occurring. Thus, these conditions permit, enhance, facilitate, and/or are conducive to the event.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

In the description herein particular embodiments may be described in isolation for clarity. Unless otherwise expressly specified that the features of a particular embodiment are incompatible with the features of another embodiment, certain embodiments can include a combination of compatible features described herein in connection with one or more embodiments.

BRIEF DESCRIPTION OF THE FIGURES

The following detailed description of illustrative embodiments of the present disclosure may be best understood when read in conjunction with the following drawings.

FIG. 3A; Chromosomal address of MELS_2191, the gene for targeted deletion. FIG. 3B; Plasmid pLAR179 containing a nonfunctional pBC1 origin of replication, the cat gene, and sites for homologous recombination for marker replacement of MELS_2191. Transformants were selected on RCM+thiamphenicol, and subsequently counter-selected with RCM+5-FU.

FIG. 4A; plasmid pLAR179 containing a copy of upp, and a copy of the cat gene flanked by sites for homologous recombination for marker replacement of MELS_0742 on the *M. elsdenii* chromosome. Transformants were selected on RCM+thiamphenicol, and then counter-selected with RCM+5-FU while maintaining positive selection for the cat gene. Plasmid was resolved via single-colony isolation in the presence of thiamphenicol. FIG. 4B; chromosomal address of MELS_0742 after targeted marker replacement.

FIG. 7A; chromosomal address of MELS_RS04415, the gene for targeted deletion. FIG. 7B; plasmid pMRW003 containing a copy of the cat gene flanked by sites for homologous recombination for marker replacement of MELS_RS04415 on the *M. elsdenii* chromosome. Transformants were selected on thiamphenicol for plasmid integration, and then counter-selected with 5-FOA for plasmid loss and pyrF deletion.

DETAILED DESCRIPTION

Figure 1:
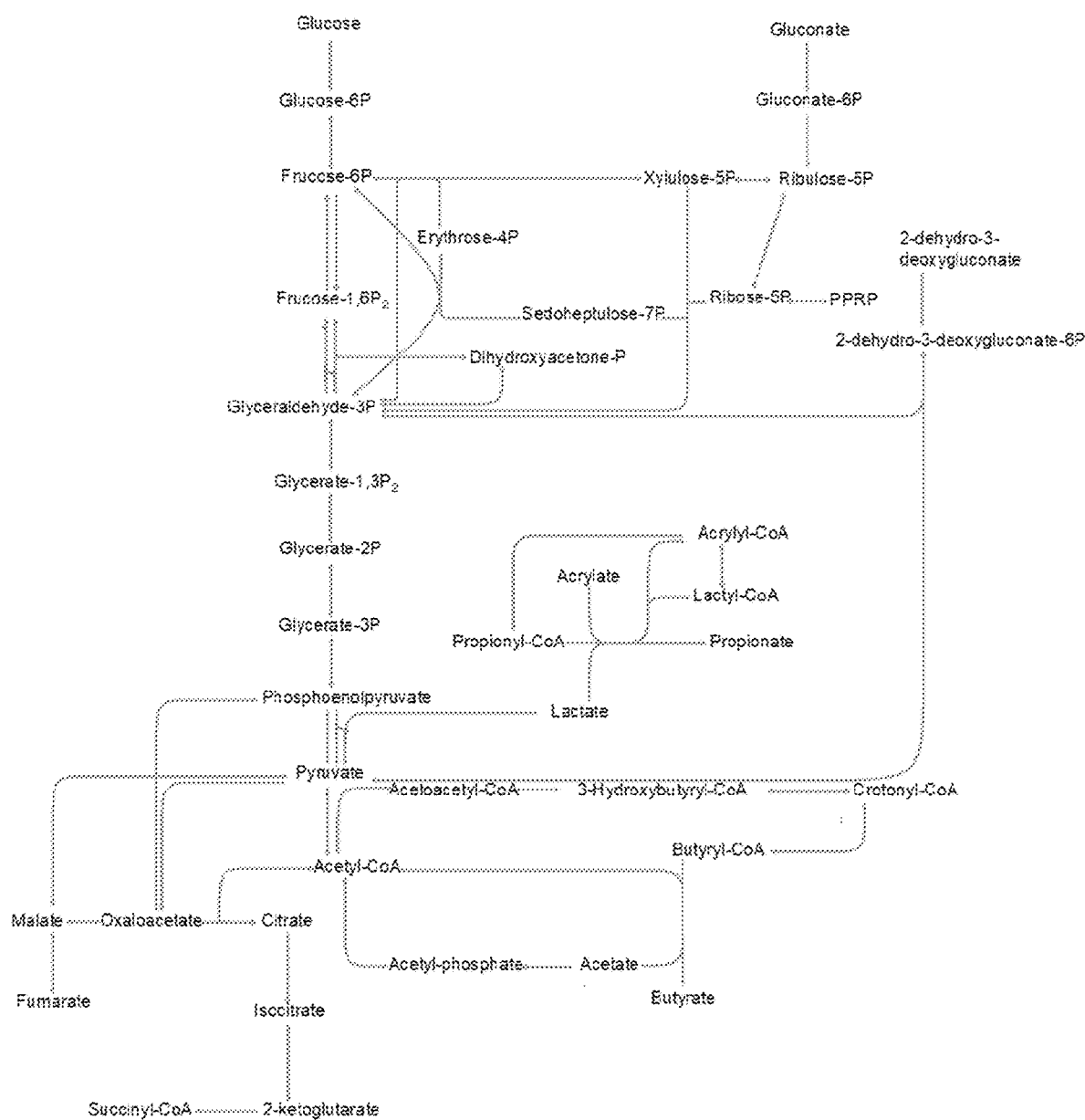
FIG. 1 shows a metabolic reconstruction of central carbon metabolism of *M. elsdenii*.

The present disclosure provides microbes, compositions, and methods useful for increasing microbial production of longer chain organic acids. The disclosure includes metabolically engineering a microbial host. The microbial host is engineered to increase carbon flux to butyryl-CoA and/or hexanoyl-CoA, to produce increased amounts of butyrate and/or hexanoate, or a combination thereof. The microbial host can be further metabolically engineered to convert butyryl-CoA to butyraldehyde and butanol, hexanoyl-CoA to hexanaldehyde and hexanol, or a combination thereof. The microbial host can also be further metabolically engineered to produce other molecules derived from the chain elongation pathway. Recombinant microbes can be referred to herein as "metabolically engineered" microbes when the genetic engineering is directed to disruption or alteration of a metabolic pathway so as to cause a change in the microbe's metabolism compared to a comparable control.

Recombinant Microbes

A microbial host that is used to engineer a recombinant microbe of the present disclosure is a member of the genus *Megasphaera*. Examples of members of the genus *Megasphaera* include *M. hominis*, *M. cerevisiae*, *M. elsdenii*, *M. micronuciformis*, *M. paucivorans*, and *M. sueciensis*. *Megasphaera* spp., are readily available. In one embodiment, the *Megasphaera* is *M. elsdenii*, and in one embodiment the *M. elsdenii* microbial host that is used to engineer a recombinant microbe is ATCC 25940. Methods for metabolically engineering a *Megasphaera* sp. are described herein.

A recombinant *Megasphaera* microbe of the present disclosure includes one or more mutations designed to increase carbon flux towards the targeted products butyrate (the straight-chain alkyl carboxylic acid with the chemical formula $CH_3(CH_2)_2CO_2H$, also referred to as butyric acid) and/or hexanoate (the straight-chain alkyl carboxylic acid with the chemical formula $CH_3(CH_2)_4CO_2H$, also referred to as hexanoic acid). The increased carbon flux towards the targeted products butyrate and/or hexanoate can be referred to as increased carbon flux to butyryl-CoA and/or hexanoyl-CoA, an intermediate step in the pathway to butyrate and/or hexanoate.

In one embodiment, a recombinant *Megasphaera* microbe, such as *M. elsdenii*, includes a mutation, such as a deletion, of a coding region encoding a CoA-transferase. Examples of CoA-transferases include those encoded by the coding regions MELS_0742, MELS_0464, and MELS_0034 of *M. elsdenii* ATCC 25940. MELS_0742 and MELS_0464 encode a propionate CoA transferase, and MELS_0034 encodes an acetate CoA/Acetoacetate CoA-transferase alpha subunit. In another embodiment, a recombinant *Megasphaera* sp., such as *M. elsdenii*, includes a mutation, such as a deletion, of a coding region encoding a member of the glyoxalase family, for instance MELS_0743. In another embodiment, a recombinant *Megasphaera* sp., such as *M. elsdenii*, includes a mutation, such as a deletion, of a coding region encoding a lyase such as lactoyl-CoA dehydratase subunit alpha, for instance MELS_0745. When a *Megasphaera* sp. other than *M. elsdenii* ATCC 25940 is used, closely related CoA-transferases, glyoxalases, and lyases can be identified using routine methods such as homology searches or RNAseq and proteomic analyses, and mutations of one or more coding regions can be engineered into the microbe using the methods described herein.

A recombinant *Megasphaera* microbe can include reduced expression of a propionyl-CoA transferase. In one or more embodiments, when the microbe is *M. elsdenii* ATCC 25940, the mutation is in the coding region MELS_0742. For instance, *M. elsdenii* ATCC 25940 was found to include four coding regions encoding putative propionate-CoA transferases, MELS_0742, MELS_0464, MELS_1631, and MELS_1130, but analysis of expression suggested that MELS_0742 was most highly expressed. Subsequent deletion of MELS_0742 resulted in a recombinant *M. elsdenii* with undetectable propionate-CoA transferase activity as inferred from fermentation profile data (Example 1).

A recombinant *Megasphaera* microbe having a mutation in one or more coding regions described herein can have increased carbon flux to butyryl-CoA, hexanoyl-CoA, or the combination thereof. In one or more embodiments, a recombinant *Megasphaera* described herein can produce increased amounts of butyrate, hexanoate, or the combination thereof, compared to a comparable control microbe. In one or more embodiments, a recombinant *Megasphaera* described herein can be further engineered to convert butyryl-CoA to butanol, hexanoyl-CoA to hexanol, or the combination thereof, and likely increased production of other molecules of longer chain length. In one or more embodiments, a recombinant *Megasphaera* described herein can consume increased amounts of acetate compared to a comparable control microbe. As used herein, a comparable control microbe is a microbe that is genetically identical to the recombinant *Megasphaera* except for the mutation or mutations being evaluated. The increased production of butyrate and/or hexanoate can be observed when the recombinant *Megasphaera* is grown on lactate (also referred to as lactic acid). In some embodiments, increased production of butyrate and/or hexanoate is not observed when the recombinant *Megasphaera* is grown on glucose. The increase of each of butyrate and/or hexanoate can be at least 2-fold, at least 4-fold, at least 6-fold, at least 8-fold, at least 10-fold, at least 100-fold, at least 1000-fold, or more compared to a comparable control microbe. In one or more embodiments, the increase of each of butyrate and/or hexanoate is no greater than 10,000-fold compared to a comparable control microbe. In some embodiments there is not a theoretical maximum fold-increase. For instance, where a microbe is engineered to produce a new compound that is not produced at detectable levels by the comparable control, the fold-increase can be extremely high even if the absolute amount of the new compound did not increase substantially. The increased consumption of acetate can be observed when the recombinant *Megasphaera* is grown on lactate (also referred to as lactic acid). In some embodiments, increased consumption of acetate is not observed when the recombinant *Megasphaera* is grown on glucose. The increase of acetate consumption can be at least 2-fold, at least 4-fold, at least 6-fold, at least 8-fold, at least 10-fold, at least 100-fold, at least 1000-fold, or more compared to a comparable control microbe.

A recombinant *Megasphaera* microbe having reduced propionate-CoA transferase activity produces decreased amounts of valerate. The presence of decreased amounts of valerate was surprising, as the expected result was a much greater decrease in valerate or no detectable valerate. The enzyme deleted, MELS_0742, is thought to be responsible also for the lactate conversion to lactoyl-CoA. The inventors predicted interrupting this reaction would interrupt the entire acrylate cycle, which provides the propionyl-CoA that leads to valerate production.

Figure 2:
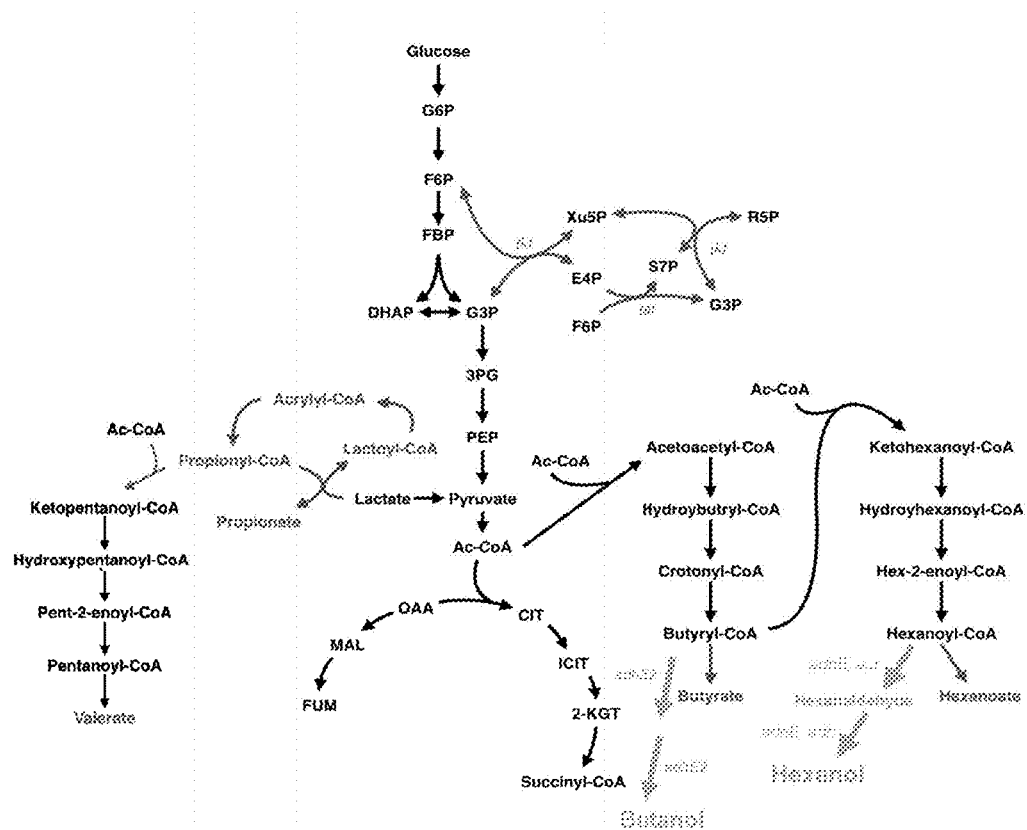
FIG. 2 shows an adaptation of predicted *M. elsdenii* ATCC 25940 metabolic map.

A model was constructed using the Department of Energy (DOE) KBase and represents glucose fermentation to butyrate and lactate fermentation to butyrate and propionate (FIG. 1). A map adaptation was constructed from the metabolic reconstruction of central carbon metabolism (FIG. 2). The map adaptation represents steps to target in the engineering of *Megasphaera*, such as *M. elsdenii*, to alter its native metabolism to genetically funnel carbon towards longer chain-length targets such as butyryl-CoA and/or hexanoyl-CoA, enabling increased production of butyrate and hexanoate. Using the constructed map and the genomic DNA sequence for *M. elsdenii*, several coding regions annotated as putative acyl-CoA transferase genes were identified. The inventors predict that mutations in one or more of these coding regions will increase flux within *Megasphaera* sp. towards longer chain-length targets such as butyrate and hexanoate. Examples of coding regions that can be targeted for mutation, in addition to those discussed herein, include MELS_0034, MELS_0437, MELS_0464, MELS_0430, MELS_0033, MELS_0341, MELS_1130, and MELS_1631. The mutation can be any mutation that reduces expression of the protein encoded by a coding region, or a mutation that reduces the activity of the protein, including a point mutation an insertion, or a deletion. A recombinant *Megasphaera* having a mutation in one or more of a coding region described herein can produce, or is expected to produce, increased amounts of butyrate, hexanoate, or the combination thereof, compared to a comparable control microbe. Accordingly, the present disclosure includes a recombinant *Megasphaera*, such as *M. elsdenii*, that includes a mutation in one or more of the coding regions described herein, in any combination. In one embodiment, a recombinant *Megasphaera* includes a mutation in a coding region encoding a propionyl-CoA transferase, such as a mutation in the coding region MELS_0742.

In one embodiment, a recombinant *Megasphaera* microbe, such as *M. elsdenii*, includes one or more mutations in coding regions responsible for the acrylate cycle pathway. The inventors used the map adaptation and the genomic DNA sequence for *M. elsdenii* to identify a cluster of several coding regions annotated as responsible for the acrylate cycle pathway. The inventors predict that mutations in these coding regions will increase flux within *Megasphaera* sp. towards longer chain-length targets such as butyryl-CoA and/or hexanoyl-CoA, leading to increased production of butyrate and hexanoate. The cluster of locus tags that will be targeted for mutation include MELS_0742-0747. The mutation can be any mutation that reduces expression of the protein encoded by a coding region, or a mutation that reduces the activity of the protein, including a point mutation, an insertion or a deletion. A recombinant *Megasphaera* having a mutation in one or more of these coding regions involved in the acrylate cycle pathway can produce increased amounts of butyrate, hexanoate, or the combination thereof, compared to a comparable control microbe. Accordingly, the present disclosure includes a recombinant *Megasphaera*, such as *M. elsdenii*, that includes a mutation in one or more of the putative acrylate cycle pathway genes.

Thus, a recombinant *Megasphaera* microbe disclosed herein includes a mutation in one or more of the following coding regions, in any combination: MELS_0742, MELS_0034, MELS_0437, MELS_0464, MELS_0430, MELS_0033, MELS_0341, MELS_1130, MELS_1631, MELS_0742, MELS_0743, MELS_0744, MELS_0745, MELS_0746, or MELS_0747.

In one embodiment, a recombinant *Megasphaera* microbe includes a mutation, such as a deletion, of a coding region encoding uracil phosphoribosyltransferase (Upp). An example of one upp coding region is MELS_2191. Uracil phosphoribosyltransferase converts the uracil analogue, 5-fluorouracil (5-FU), to the toxic product fluorodeoxyuridylate which kills growing microbes that are synthesizing uracil. As described herein, mutants of upp are, therefore resistant to 5-FU, providing 5-FU resistance as a counter selectable marker (Guss and Riley, US Published Patent Application No. 2021/0024965).

In one embodiment, a recombinant *Megasphaera* microbe includes a mutation, such as a deletion, of a coding region encoding orotidine-5'-phosphate decarboxylase (PyrF). An example of one pyrF coding region is MELS_RS04415. Deletion and complementation of orotidine-5'-phosphate decarboxylase (pyrF) in *Megasphaera*, such as *M. elsdenii* allows for counter-selection of transformants growing in media containing uracil. In the presence of 5-Fluoroorotic acid (5-FOA), the pyrE gene product orotate phosphoribosyltransferase adds a phosphate group via phosphoribosyl pyrophosphate to 5-FOA becoming 5'-fluoroorotidine monophosphate and the substrate for the pyrF gene. pyrF cleaves the carboxylic group from 5'-fluoroorotidine monophosphate creating 5'-fluorouridine monophosphate (5'-FUMP), a toxic analog of uridine monophosphate and a precursor to both the RNA nucleotide uracil and the DNA nucleotide thymine. The addition of fluorine at the 5' carbon becomes a lethal inhibitor to thymidylate synthetase, preventing the methylation and conversion of 5'-fluorouracil to thymidine. These toxic nucleotide analogs prevent the translation of RNA, the replication of DNA, and ultimately cause cell death. Nonconservative pyrF mutants are uracil auxotrophs and resistant to 5-FOA. The inventors have established 5-FOA minimal inhibitory concentrations (MICs) in Reinforced clostridial medium (RCM), a rich complex media, at 1 mg/mL and 2.5 mg/mL in liquid and solid media, respectively. 5-FOA allows for counter-selection with sufficient uracil present in the growth medium.

In one embodiment a recombinant *Megasphaera* microbe includes an exogenous coding region encoding a bifunctional aldehyde-alcohol dehydrogenase. An example of a coding region encoding aldehyde-alcohol dehydrogenase is adhE2. An adhE2 coding region can be obtained from a member of the genus *Clostridium*, such as *C. acetobutylicum*. Examples of adhE2 coding regions and AdhE2 proteins, and engineering *M. elsdenii* to include adhE2, are described in Guss and Riley (US Published Patent Application No. 2021/0024965). A bifunctional aldehyde-alcohol dehydrogenase can catalyze the production of butanol from butyryl-CoA.

In one embodiment a recombinant *Megasphaera* microbe includes an exogenous coding region encoding an acyl-CoA reductase. An example of a coding region encoding acyl-CoA reductase is acr. An acr coding region can be obtained from a member of the genus *Clostridium*, such as *C. acetobutylicum, C. carboxidivorans*, and *C. saccharoperbutylacetonicum*. An acyl-CoA reductase can catalyze the conversion of hexanoyl-CoA to hexanaldehyde.

In one embodiment a recombinant *Megasphaera* microbe includes an exogenous coding region encoding an alcohol dehydrogenase. An example of a coding region encoding alcohol dehydrogenase is adh. An adh coding region can be obtained from a member of the genus *Clostridium*, such as *C. acetobutylicum, C. carboxidivorans*, and *C. saccharoperbutylacetonicum*. An alcohol dehydrogenase can catalyze the conversion of hexanaldehyde to hexanol.

Methods of Making a Recombinant *Megasphaera* Microbe

*Megasphaera* sp. typically include robust restriction systems that cleave a DNA polynucleotide introduced into a *Megasphaera* sp. This has prevented the establishment of methods for genetic analysis of *Megasphaera* sp. Provided herein are methods for genetically engineering *Megasphaera*, including *M. elsdenii*, to construct the recombinant *Megasphaera* described herein.

Microbial strains have been created that methylate DNA for introduction into *Megasphaera* cells and the successful identification of transformants. The methylated DNA obtained from the methylating microbial strains can be introduced into *Megasphaera* cells and is protected from the *Megasphaera* restriction systems. One example of a methylating microbial strain includes the coding regions MELS_0050-0051 and MELS_1615-1616. In one embodiment, a methylating microbial strain expressing these coding regions is an *E. coli* such as TOP10 (ThermoFisher) further genetically modified to be dcm−. The TOP10 strain can be further modified to include a poly-attB cassette, for instance integrated at the Hong Kong phage attachment locus, and MELS_0050-0051 integrated at the R4 site of the poly-attB and MELS_1615-1616 integrated at the lambda attB locus. The proteins encoded by MELS_0050-0051 and MELS_1615-1616 are useful in preparing DNA for transformation into *M. elsdenii* ATCC 25940 and potentially other *Megasphaera* spp. Methylating microbial strains are described in Guss and Riley (US Patent Application No. 2021/0024965).

Also provided herein is a recombinant *Megasphaera* that has been engineered to introduce a mutation to result in decrease expression of one or more of the coding regions MELS_0050, MELS_0051, MELS_1615, or MELS_1616. In one embodiment, a recombinant *Megasphaera* includes a mutation of both MELS_0050 and MELS_0051, both MELS_1615 and MELS_1616, or a mutation of MELS_0050, MELS_0051, MELS_1615, and MELS_1616. The mutation can be any mutation that reduces expression of the protein encoded by the coding region, or a mutation that reduces the activity of the protein, including a point mutation, an insertion, or a deletion. A recombinant *Megasphaera* including a mutation in one or more of these coding regions has a reduced or inactive restriction system, and DNA can be transformed into such a recombinant *Megasphaera* with the expectation that transformants will be identified.

Accordingly, producing a recombinant *Megasphaera*, for instance *M. elsdenii*, includes transforming with DNA that has been obtained from a methylating microbial strain. DNA used to transform *Megasphaera* sp. is typically in the form of a vector. A vector is a replicating polynucleotide, such as a plasmid, to which another polynucleotide may be attached so as to bring about the replication of the attached polynucleotide. The term vector includes, but is not limited to, plasmid vectors, viral vectors, cosmid vectors, or artificial chromosome vectors. Typically, a vector is capable of replication in a microbial host, for instance *E. coli*. In some embodiments a vector is capable of replication in a *Megasphaera* sp. In some embodiments the vector is a plasmid. Origins of replication that are useful in *Megasphaera* include, but are not limited to, those present in the plasmids pIM13 (Projan et al., 1987), pBC1 (De Rossi et al., 1992), and pVJL1 (Liu et al., 2012).

DNA used to transform a *Megasphaera* sp. optionally includes one or more marker sequences, which typically encode a molecule that inactivates or otherwise detects or is detected by a compound in the growth medium. For example, the inclusion of a marker sequence can render the transformed microbe resistant to an antibiotic, or it can confer compound-specific metabolism on the transformed microbe. Examples of marker sequence that confer resistance and can be used in *Megasphaera* sp. include those encoding resistance to chloramphenicol and to erythromycin.

In one embodiment, the *Megasphaera* sp. to be transformed includes reduced expression, such as undetectable expression, of an upp coding region. In one embodiment, the upp coding region is MELS_2191. Use of a recipient *Megasphaera* sp. with an upp mutation is helpful in engineering targeted mutations, such as deletions, of specific coding regions, or targeted insertions of DNA, such as a coding region (Guss and Riley, US Published Patent Application No. 2021/0024965). The polynucleotide used to transform a *Megasphaera* sp. includes an upp coding region, e.g., MELS_2191, which encodes uracil phosphoribosyltransferase and converts 5-fluorouracil (5-FU), to the toxic product fluorodeoxyuridylate, which kills growing microbes. For instance, transformation of a *Megasphaera* sp. with a plasmid containing sequences of DNA sharing homology to sequences flanking a coding region targeted for deletion can result in the integration of the plasmid into the microbe's chromosome to produce a specific genetic lesion. If the *Megasphaera* sp. includes a deletion of upp and the vector includes an upp coding region, incubating the transformants in 5-FU can counter-selection against the integrated vector (see Example 1). Accordingly, the present disclosure also includes methods for using a *Megasphaera* having an upp mutation, including methods for constructing a *Megasphaera* having a targeted mutation. The targeted mutation can be the production of a deletion of the target coding region. The production of a deletion greatly reduces the likelihood of reversion.

A method for using an upp-*Megasphaera* to construct a *Megasphaera* having a targeted mutation includes transforming the *Megasphaera* with a plasmid that includes an upp coding region that will complement the upp mutation. The plasmid is replication incompetent in the recipient *Megasphaera*. The plasmid also includes a mutagenic cassette. A mutagenic cassette is designed to target a specific location, typically a coding region, where a mutation is to be introduced.

In one embodiment, the *Megasphaera* sp. to be transformed includes reduced expression, such as undetectable expression, of a pyrF coding region. In one embodiment, the pyrF coding region is MELS_RS04415. Use of a recipient *Megasphaera* sp. with a pyrF mutation is helpful in engineering targeted mutations, such as deletions, of specific coding regions, or targeted insertions of DNA, such as a coding region (see, for instance, Lipscomb et al., 2016, Applied and Environmental Microbiology, 82(14):4421-4428). The polynucleotide used to transform a *Megasphaera* sp. includes a pyrF coding region, e.g., MELS_RS04415, which encodes orotidine-5'-phosphate decarboxylase and converts 5-Fluoroorotic acid (5-FOA) to a toxic product that kills the cells. Deleting pyrF results in a strain that is a uracil auxotroph resistant to 5-FOA, allowing prototrophic selection and counter-selection of the wild-type pyrF. For instance, transformation of a *Megasphaera* sp. with a plasmid containing sequences of DNA sharing homology to sequences flanking a coding region targeted for deletion can result in the integration of the plasmid into the microbe's chromosome to produce a specific genetic lesion. If the *Megasphaera* sp. includes a deletion of pyrF and the vector includes a pyrF coding region, incubating the transformants in 5-FOA can counter-selection against the integrated vector. Accordingly, the present disclosure also includes methods for using a *Megasphaera* having a pyrF mutation, including methods for constructing a *Megasphaera* having a targeted mutation. The targeted mutation can be the production of a deletion of the target coding region. The production of a deletion greatly reduces the likelihood of reversion.

A method for using a pyrF-*Megasphaera* to construct a *Megasphaera* having a targeted mutation includes transforming the *Megasphaera* with a plasmid that includes a pyrF coding region that will complement the pyrF mutation. The plasmid is replication incompetent in the recipient *Megasphaera*. The plasmid also includes a mutagenic cassette. A mutagenic cassette is designed to target a specific location, typically a coding region, where a mutation is to be introduced.

The mutagenic cassette includes two distinct DNA sequences that will permit homologous recombination between the plasmid and the microbe's chromosome. The two distinct DNA sequences typically flank the targeted coding region in the microbe's chromosome. On the plasmid, the two distinct DNA sequences flank the lesion that is to be introduced into the chromosome. The lesion, in combination with the two distinct DNA sequences, can be one that will result in deletion of the coding region. The mutagenic cassette also includes a marker, such as a coding region encoding an antibiotic marker, present within the lesion. Optionally, the mutagenic cassette also includes two attachment sites that flank the lesion. In one embodiment, the structure of a mutagenic cassette is first homologous DNA sequence-first attachment site-lesion/marker-second attachment site-second homologous DNA sequence. The attachment sites are sequence that can be identified by a recombinase, such as an integrase and, in the presence of a suitable recombinase, the region between the attachment sites—the marker—can be removed from the chromosome.

Following transformation, recipients of the plasmid are selected using the marker present with the lesion. The result is transformants that are likely to include the plasmid integrated in the chromosome by virtue of a crossover event between one of the two DNA sequences and the appropriate sequences on the microbe's chromosome. After selection for successful transformants, subsequent exposure of the transformants to 5-FU or 5-FOA selects for a second crossover event that eliminates the upp coding region or the pyrF coding region and the plasmid sequences, resulting in the insertion of the lesion, such as a deletion, of the targeted coding region. The coding region encoding the marker can then be removed by use of a recombinase.

A *Megasphaera* sp. can also be engineered to include an exogenous polynucleotide, such as, but not limited to, a bifunctional aldehyde-alcohol dehydrogenase such as one encoded by adhE2, an acyl-CoA reductase such as one encoded by acr, or an alcohol dehydrogenase such as one encoded by adh. Methods for use of upp and use of pyrF to engineer insertions into microbe are described in Guss and Riley (US Published Patent Application No. 2021/0024965) and (Lipscomb et al., 2016, Applied and Environmental Microbiology, 82(14):4421-4428). A coding region present on a polynucleotide that is to be introduced into a *Megasphaera* sp. can be codon optimized for expression in the *Megasphaera* sp.

Methods for transformation of *Megasphaera* spp. include electroporation. Examples of producing electrocompetent *Megasphaera* spp. are described in Example 1 and in Guss and Riley (US Patent Application No. 2021/0024965).

Methods of Using Recombinant *Megasphaera*

The present disclosure also includes methods of using a recombinant *Megasphaera*. In one embodiment, a method includes using a recombinant *Megasphaera* to produce butyrate and/or hexanoate. The method includes incubating a recombinant *Megasphaera* under conditions suitable for fermentation. Typically, the medium used includes lactate as the primary carbon source, and in one embodiment, the sole carbon source.

In one embodiment, the method can include further processing of the butyryl-CoA and/or hexanoyl-CoA product. For instance, if the recombinant *Megasphaera* include an exogenous coding region encoding a bifunctional aldehyde-alcohol dehydrogenase, such as adhE2, butyryl-CoA is converted to butanol (Guss and Riley, US Patent Application No. 2021/0024965). Alternatively, if the recombinant *Megasphaera* include an exogenous coding region encoding an acyl-CoA reductase, such as acr, hexanoyl-CoA is converted to hexanaldehyde, and if the recombinant *Megasphaera* also includes an exogenous coding region encoding an alcohol dehydrogenase, such as adh, hexanaldehyde is converted to hexanol.

A recombinant *Megasphaera* is incubated under anaerobic conditions and at a temperature, including but not limited to 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C. In one embodiment, the host cells are incubated at 37° C. Lactate is typically used as the carbon source for cell growth and maintenance, including the production of butyrate and/or hexanoate (e.g., 5 g/L, 44 mM). In some embodiments, such as the production of mutations, glucose can be used as the carbon source (e.g., 5 g/L, 27 mM).

Exemplary Aspects

The invention is defined in the claims. However, below there is provided a non-exhaustive listing of non-limiting exemplary aspects. Any one or more of the features of these aspects may be combined with any one or more features of another example, embodiment, or aspect described herein.

Aspect 1. A recombinant *Megasphaera* microbe genetically modified to (i) consume a greater amount of acetate, (ii) produce a greater amount of butyrate, hexanoate, or a combination thereof, than a comparable control microbe, or (iii) increase carbon flux to butyryl-CoA and/or hexanoyl-CoA than a comparable control microbe, or a combination thereof, wherein the recombinant *Megasphaera* microbe comprises a mutation of a CoA-transferase coding region, a glyoxalase coding region, or a lyase coding region.

Aspect 2. The recombinant *Megasphaera* microbe of Aspect 1, wherein the recombinant *Megasphaera* microbe is *M. elsdenii*.

Aspect 3. The recombinant *Megasphaera* microbe of Aspect 1 or 2, wherein the *M. elsdenii* is a modified ATCC 25940.

Aspect 4. The recombinant *Megasphaera* microbe of any one of Aspects 1-3, wherein the mutation of the CoA-transferase coding region comprises a deletion of the CoA transferase coding region.

Aspect 5. The recombinant *Megasphaera* microbe of any one of Aspects 1-4, wherein the CoA-transferase coding region encodes a propionyl-CoA transferase.

Aspect 6. The recombinant *Megasphaera* microbe of any one of Aspects 1-5, wherein propionate production by the recombinant *Megasphaera* microbe is undetectable.

Aspect 7. The recombinant *Megasphaera* microbe of any one of Aspects 1-6, wherein the propionyl-CoA transferase coding region is MELS_0742, MELS_0464, MELS_1631, or MELS_1130, or a combination thereof.

Aspect 8. The recombinant *Megasphaera* microbe of any one of Aspects 1-7, wherein the recombinant *Megasphaera* microbe comprises a mutation of at least 1, at least 2 propionyl-CoA transferase coding regions selected from MELS_0742, MELS_0464, and MELS_0034, or mutation of all 3 propionyl-CoA transferase coding regions.

Aspect 9. The recombinant *Megasphaera* microbe of any one of Aspects 1-8, wherein the mutation of the glyoxalase coding region comprises a deletion of the glyoxalase coding region.

Aspect 10. The recombinant *Megasphaera* microbe of any one of Aspects 1-9, wherein the glyoxalase coding region is MELS_0743.

Aspect 11. The recombinant *Megasphaera* microbe of any one of Aspects 1-10, wherein the mutation of the lyase coding region comprises a deletion of the lyase coding region.

Aspect 12. The recombinant *Megasphaera* microbe of any one of Aspects 1-11, wherein the lyase coding region is MELS_0745.

Aspect 13. The recombinant *Megasphaera* microbe of any one of Aspects 1-12, wherein the increase of butyrate or hexanoate is at least 2-fold greater than the comparable control microbe.

Aspect 14. The recombinant *Megasphaera* microbe of any one of Aspects 1-13, wherein the increase of acetate consumption is at least 2-fold greater than the comparable control microbe.

Aspect 15. A recombinant *Megasphaera* microbe comprising a mutation of a pyrF coding region.

Aspect 16. The recombinant *Megasphaera* microbe of any one of Aspects 1-15, wherein the mutation is a deletion of at least a portion of the pyrF coding region.

Aspect 17. The recombinant *Megasphaera* microbe of any one of Aspects 1-16, wherein the *Megasphaera* microbe is *M. elsdenii*.

Aspect 18. The recombinant *Megasphaera* microbe of any one of Aspects 1-17, wherein the *M. elsdenii* is a modified ATCC 25940.

Aspect 19. The recombinant *Megasphaera* microbe of any one of Aspects 1-18, wherein the pyrF coding region is MELS_RS04415.

Aspect 20. A method for increasing carbon flux to acetoacetyl-CoA, comprising: incubating a recombinant *Megasphaera* microbe with lactate as a carbon source under conditions suitable for replication, wherein the carbon flux to acetoacetyl-CoA in the recombinant *Megasphaera* is at a level greater than a comparable control, and, wherein the recombinant *Megasphaera* microbe comprises a mutation of a CoA-transferase coding region, a glyoxalase coding region, or a lyase coding region a mutation of a CoA-transferase.

Aspect 21. A method for producing butyrate, hexanoate, or combination thereof, comprising: incubating a recombinant *Megasphaera* microbe with lactate as a carbon source under conditions suitable for replication, wherein the recombinant *Megasphaera* produces butyrate, hexanoate, or combination thereof at a level greater than a comparable control, wherein the recombinant *Megasphaera* microbe comprises a mutation of a CoA-transferase coding region, a glyoxalase coding region, or a lyase coding region a mutation of a CoA-transferase.

Aspect 22. A method for genetically engineering a *Megasphaera*, comprising: providing the recombinant *Megasphaera* of any one of Aspects 1-19, transforming the recombinant *Megasphaera* with a plasmid comprising a pyrF coding region and a mutagenic cassette, wherein the mutagenic cassette of the plasmid comprises a marker flanked by DNA sequences, wherein the DNA sequences are selected to result in homologous recombination between the plasmid and two regions of DNA present in the recombinant *Megasphaera* that flank a coding region targeted for mutation; and incubating the transformed recombinant *Megasphaera* under conditions suitable for positive selection of the transformed recombinant *Megasphaera* and counter selection of the transformed recombinant *Megasphaera* to select for those that have lost the pyrF coding region, wherein the transformed recombinant *Megasphaera* identified by the positive and counter selection comprise a mutation of the targeted coding region.

Aspect 23. The method of Aspect 22, wherein the mutagenic cassette of the plasmid further comprises attachment sites flanking the marker, wherein the attachment sites are between the marker and the DNA sequences, and wherein the attachment sites are identified by a recombinase that can promote recombination between the two attachment sites and deletion of the marker located between the attachment sites.

Aspect 24. The method of Aspect 22 or 23, wherein the mutation of the targeted coding region comprises a deletion of the targeted coding region.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

Methods for Engineering Deletions in *Megasphaera*: Deletion of upp Gene

A coding sequence (CDS) of an *M. elsdenii* is referred to herein using one of two locus tag identifiers. One locus tag identifier has the prefix "MELLS_" followed by the number of the CDS in the *Megasphaera elsdenii* strain DSM 20460 draft genome, GenBank accession HE576794.1. The second locus tag identifier has the prefix "MELS_RS" followed by the number of the CDS in the *Megasphaera elsdenii* strain DSM 20460 complete sequence, GenBank accession NC_015873.1.

Figure 3A:
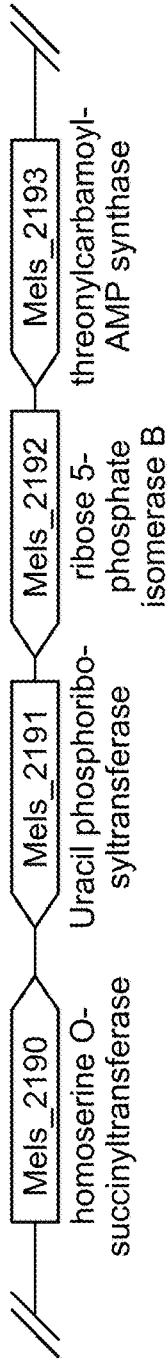
FIGS. 3A-B show schematics depicting the deletion of a CDS encoding uracil phosphoribosyltransferase MELS_2191.
Figure 3B:
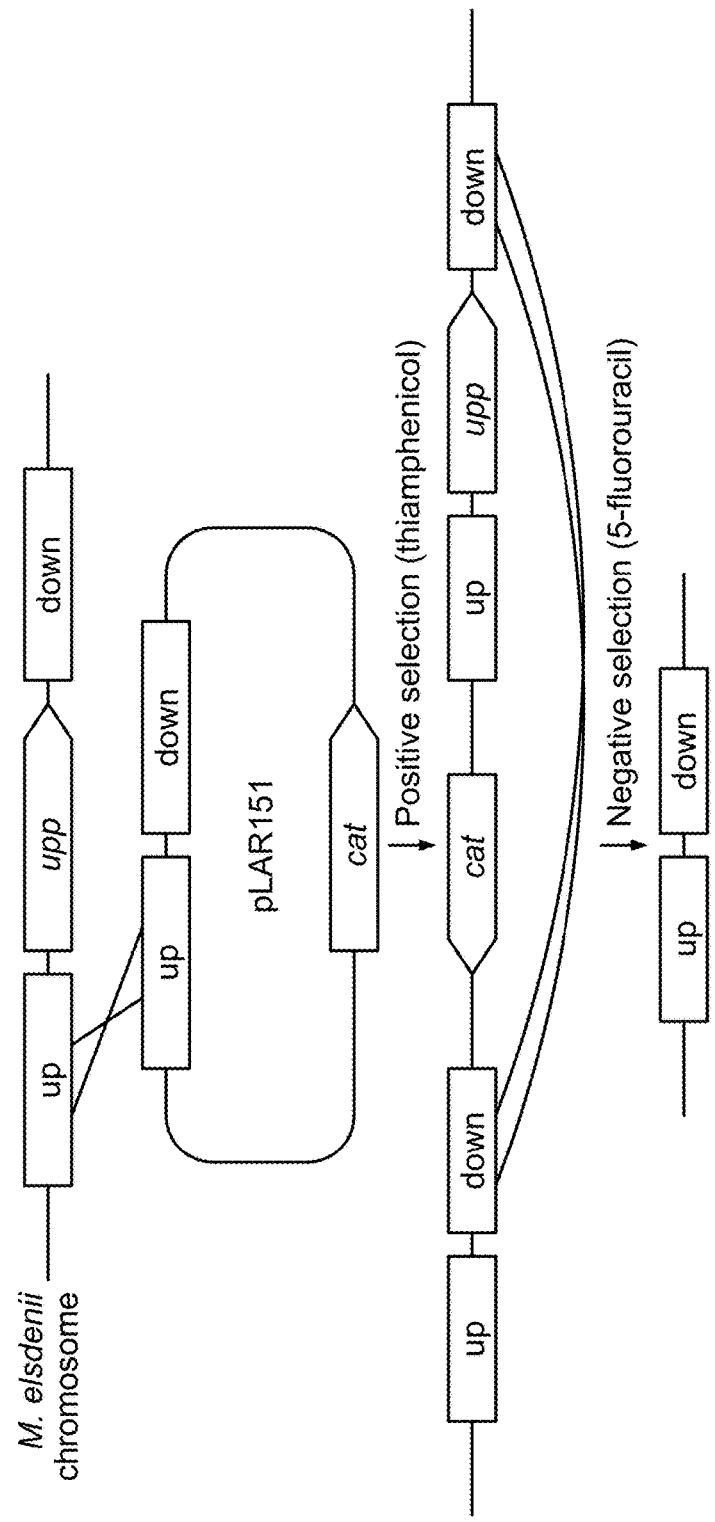

Deletion of MELS_2191, a uracil phosphoribosyltransferase (upp), in the *M. elsdenii* chromosome. To construct a deletion of MELS_2191 in the *M. elsdenii* ATCC 25940 genome (Hatmaker, 2019), plasmid pLAR151 was constructed by Gibson assembly (Table 1) via an intermediate plasmid, pLAR147. The pBC1 origin of replication was amplified from the pBC1 plasmid (DeRossi, 1992) cloned in place of pIM13 in the shuttle plasmid pMTL82151 (Heap, 2009), resulting in plasmid pLAR147. Then, 490 bp each that are DNA regions upstream and downstream of the upp gene (MELS_2191) were amplified and cloned into the MCS of pLAR147, resulting in the plasmid pLAR151. Additionally, a point mutation was inadvertently obtained in the pBC1 origin of replication, potentially rendering it non-functional. All PCR amplifications were performed using Phusion Master Mix (Thermo Fisher). The plasmid pLAR151 was transformed into *E. coli* strain AG4157 (Table 1) which expresses two methyltransferases and their corresponding specificity subunits (MELS_0051-0052, MELS_1615-1616) from *M. elsdenii* cloned into the *E. coli* chromosome. Electrocompetent cells of *M. elsdenii* ATCC 25940 were prepared (Guss 2021), and methylated plasmid DNA was subsequently isolated and used to transform *M. elsdenii* ATCC 25940 according to the transformation procedure of Guss 2021. Transformants were selected on RCM (HIMEDIA) agar plates with 5 µg/mL thiamphenicol (TM) incubated for 72 hours. Colonies were picked into RCM (BD Difco) with 5 µg/mL TM and incubated overnight. The liquid cultures were passaged into RCM (HIMEDIA) liquid cultures and subsequently plated in RCM (BD Difco) with 20 µg/mL 5-fluorouracil. The plates were incubated overnight, and colonies were streaked on RCM plates. Single colonies were picked into RCM (HIMEDIA) and PCR screened for the chromosomal deletion of upp (FIGS. 3A and 3B).

TABLE 1

Strains and plasmids

| Strains & plasmids | Genotype/phenotype | Source |
|---|---|---|
| *E. coli* | | |
| AG4157 | Top10 dcm- HK::poly-att-cassette R4::MELS_0051-52 λ::MELS_1616-17 | this study |
| *M. elsdenii* | | |
| AG5855 | ATCC 29540 Δupp | this study |
| JWME04 | ATCC 29540 Δupp ΔMELS_0742::phiC31-cat-phiC31 | this study |
| plasmids | | |
| pMTL85141 | Shuttle vector containing pIM13 ori | Heap 2009 |
| pMTL82151 | Shuttle vector containing pIM13 ori | Heap 2009 |
| pLAR147 | Intermediate plasmid containing pBC1 ori | this study |
| pLAR151 | upp deletion vector containing potentially nonfunctional pBC1 ori | this study |
| pLAR179 | MELS-0742 deletion vector | this study |

TABLE 2

Primers used in this study

| Primer | Sequence | Description |
|---|---|---|
| NW062 | TACGTCTATCGGCTTTGTCAGCAGCG (SEQ ID NO: 1) | Screening primers located inside MELS_0742 gene |
| NW063 | TTTTCAAGCCGCCAGCCGTGAA (SEQ ID NO: 2) | |
| NW066 | TCAAAGGCCTCCGCAATACGATCAT (SEQ ID NO: 3) | Screening primers located outside of flanking regions of MELS_0742 gene |
| NW067 | ACATCGTCCACTTCGAAGGCGATGT (SEQ ID NO: 4) | |
| NW065 | GAACTTGAATTGCCAAAGGAAGT (SEQ ID NO: 5) | Screening primer located inside the cat gene used in marker replacement of Mels_0742 |

TABLE 2-continued

Primers used in this study

| Primer | Sequence | Description |
|---|---|---|
| 147_backbone_F | gtaagctagcTCAGATCCTTCCGTATT (SEQ ID NO: 6) | Primers to amplify backbone of pMTL85121, excluding pIM13 ori |
| 147_backbone_R | aggtgtccatGCAGGTAAACCTCCTT (SEQ ID NO: 7) | |
| 147_insert_F | gtttacctgcATGGACACCTACGCG (SEQID NO: 8) | Primers to amplify pBC1 ori from pBC1 plasmid for construction of pLAR147 |
| 147_insert_R | aaggatctgaGCTAGCTTACGCCG (SEQID NO: 9) | |
| upp_up_F | CGCCTTTGAGTGAGCTGATACCGCACATCCAAGTCTATAA TACGCCGCAGC (SEQ ID NO: 10) | Primers to amplify 490 bp upstream of MELS_2191, upp, for construction of pLAR147 |
| upp_down_R | CATGCTCCAACAGCAAAAAGGAAAATTAGTACTCGGCGCC GATCA (SEQ ID NO: 11) | |
| 151_backbone_F | TCCTTTTTGCTGTTGGAGCATG (SEQ ID NO: 12) | Primers to amplify and linearize the backbone of pLAR151 from pLAR149 for construction of pLAR151 |
| 151_backbone_R | GCGGTATCAGCTCACTCAAAGGC (SEQ ID NO: 13) | |
| upp_up_R | GATTTCACACTAATCGTTCATCGACGTA (SEQ ID NO: 14) | Primers to amplify 490 bp downstream of MELS_2191, upp, for construction of pLAR151 |
| upp_down_F | TGAACGATTAGTGTGAAATCTCCTTTCCTA (SEQ ID NO: 15) | |
| 179_backbone_F | aagcctggttgcatgCTTCAGGTTTGTCTGTAACT (SEQ ID NO: 16) | Primers to amplify the backbone of pMTL85141, excluding the cat gene, for construction of pLAR179 |
| 179_backbone_R | tacttgtacgtgcatCTAAGTTCCCTCTCAAATT (SEQ ID NO: 17) | |
| 179_upp_F | tgagagggaacttagATGCACGTACAAGTAATG (SEQ ID NO: 18) | Primers to amplify MELS_2191, upp, for construction of pLAR179 |
| 179_upp_R | tcagggagatggcccTTATTTCGTGCCGA (SEQ ID NO: 19) | |
| 179_homology_F | ttcggcacgaaataaGGGCCATCTCCC (SEQ ID NO: 20) | Primers to amplify homology arm cassette containing 800 bp upstream and downstream of MELS_0742, cat gene, and phiC31 sites, for construction of pLAR179 |
| 179_homology_R | cagacaaacctgaagCATGCAACCAGGCT (SEQ ID NO: 21) | |

Results

Deletion of the *M. elsdenii* uracil phosphoribosyltransferase gene allows counter-selection of the wild type allele using 5-fluorouracil. Uracil phosphoribosyltransferase (upp) converts the uracil analogue, 5-fluorouracil (5-FU), to a toxic product, fluorodeoxyuridylate (HdUMP, Singh 2015). To test whether *M. elsdenii* was sensitive to 5-FU, cells were grown in liquid medium with 5-200 μg of 5-FU and found to be sensitive to 5 μg/mL 5-FU. Growth of the wild type strain on 5-FU selecting resistance also resulted in spontaneous mutations in this gene, indicating that it is responsible for conversion of 5-FU to FdUMP. A deletion of the uracil phosphoribosyltransferase (upp, MELS_2191) in the *M. elsdenii* chromosome resulted in a strain, AG5855, that is resistant to 50 μg/ml 5-FU. This chromosomal deletion allowed for the counter-selection of plasmids containing a copy of the wild type allele. This is the first counter-selection strategy developed in *M. elsdenii*.

Example 2

Methods for Engineering Deletions in *Megasphaera*: Deletion of a Putative Propionyl-CoA Transferase Gene Deletion of a putative propionyl CoA transferase (MELS_0742) from the *M. elsdenii* chromosome. Plasmid pLAR179 was constructed via Gibson assembly. The plasmid's backbone was amplified from plasmid pMTL85141 (Heap, 2009) to linearize the plasmid, excluding the cat gene. MELS_2191, the uracil phosphoribosyltransferase, was amplified from the *M. elsdenii* chromosome and was cloned in place of the cat gene for the purposes of counter-selection. Additionally, a cassette containing ~800 bp upstream and downstream of MELS_0742 flanking a cat gene driven by the promoter region of MELS_0747 ($P_{MELS\_0747}$) and PhiC31 attB/P sites, was synthesized by Twist Bioscience. Subsequently, the cassette was amplified and cloned into the final construct downstream of the upp gene. The plasmid was transformed into *E. coli* strain AG4157 (Table 1), and isolated. Electrocompetent cells of *M. elsdenii* ATCC 25940 were prepared (Guss 2021), and methylated plasmid pLAR179 was subsequently isolated and used to transform AG5855 (*M. elsdenii* ATCC25940

Figure 4A:
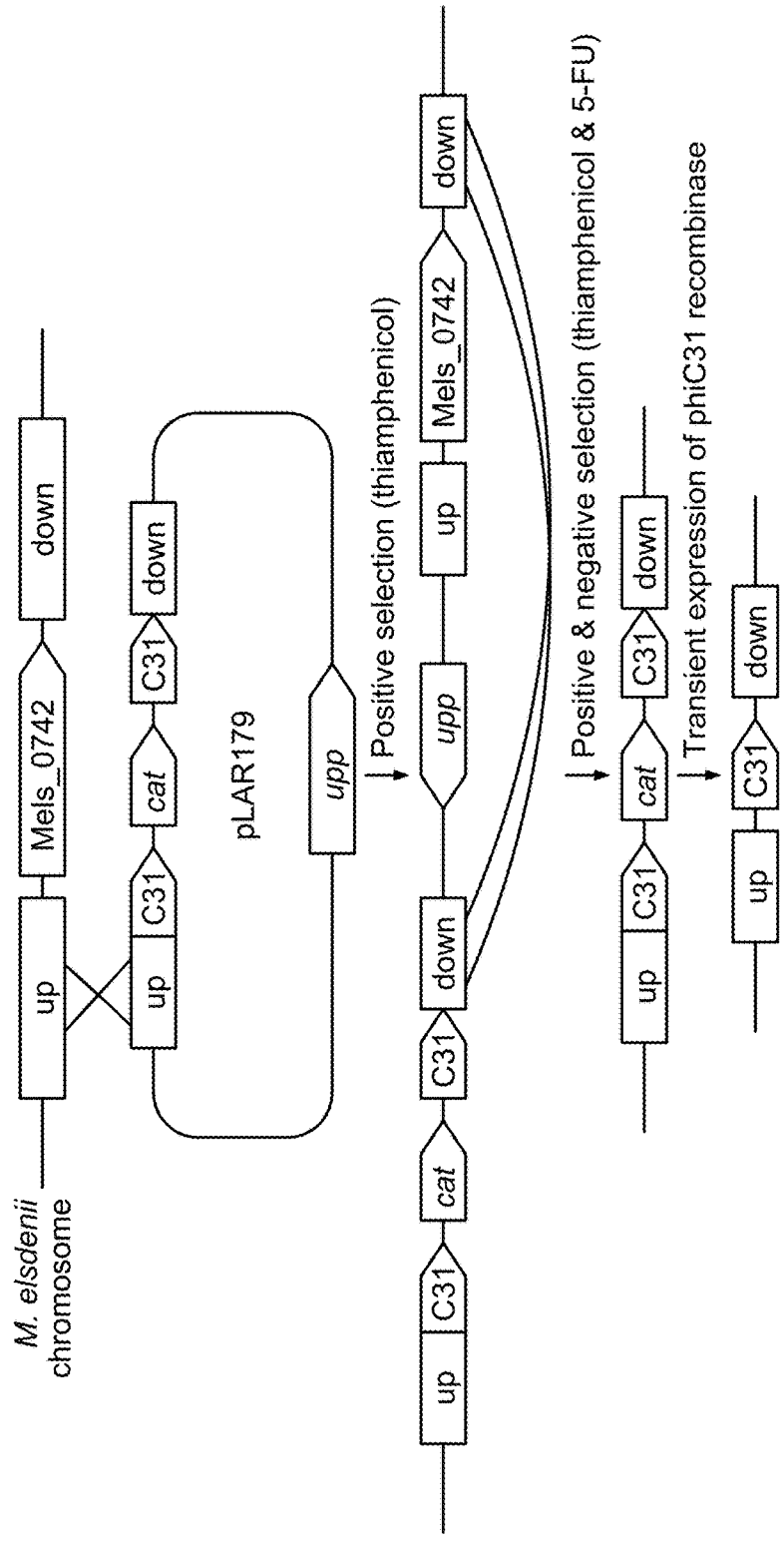
FIGS. 4A and 4B show schematics depicting the deletion of a CDS encoding a putative propionyl-CoA transferase MELS_0742.
Figure 4B:
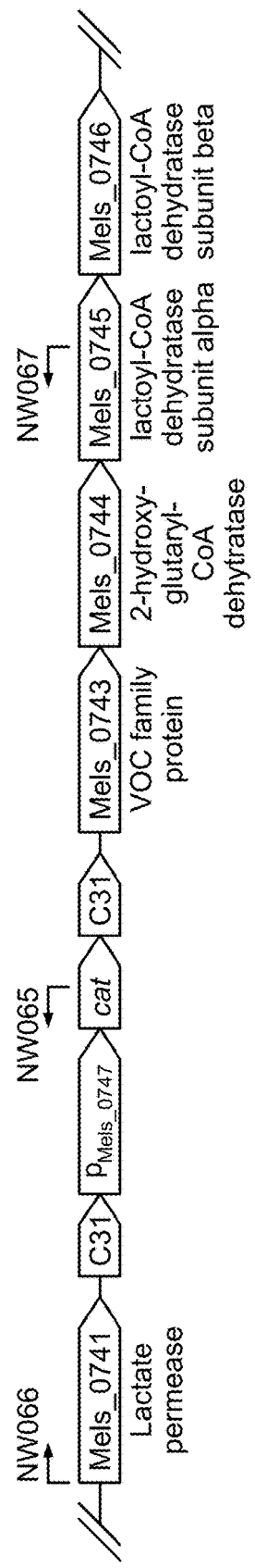

Δupp). Colonies were selected on RCM agar plates containing 5 µg/mL thiamphenicol and incubated at 37° C. for 72 hours. Colonies were picked into liquid medium containing RCM medium (Difco) with 5 µg/mL TM, incubated overnight, and then plated on RCM (Difco) with 5 µg/mL TM and 50 µg/mL 5-fluorouracil for counter-selection of the plasmid. Plates were incubated for 48 hours at 37° C. and single colonies were picked into RCM (Difco) liquid medium with 5 µg/mL TM and screened for the marker-replacement (FIGS. 4A and 4B). Three single colony purifications were needed to generate a pure culture of the deletion from the initial merodiploid.

Results

Deletion of a putative propionyl-CoA reductase gene results in loss of propionate production and decreased valerate production.

Figure 5:
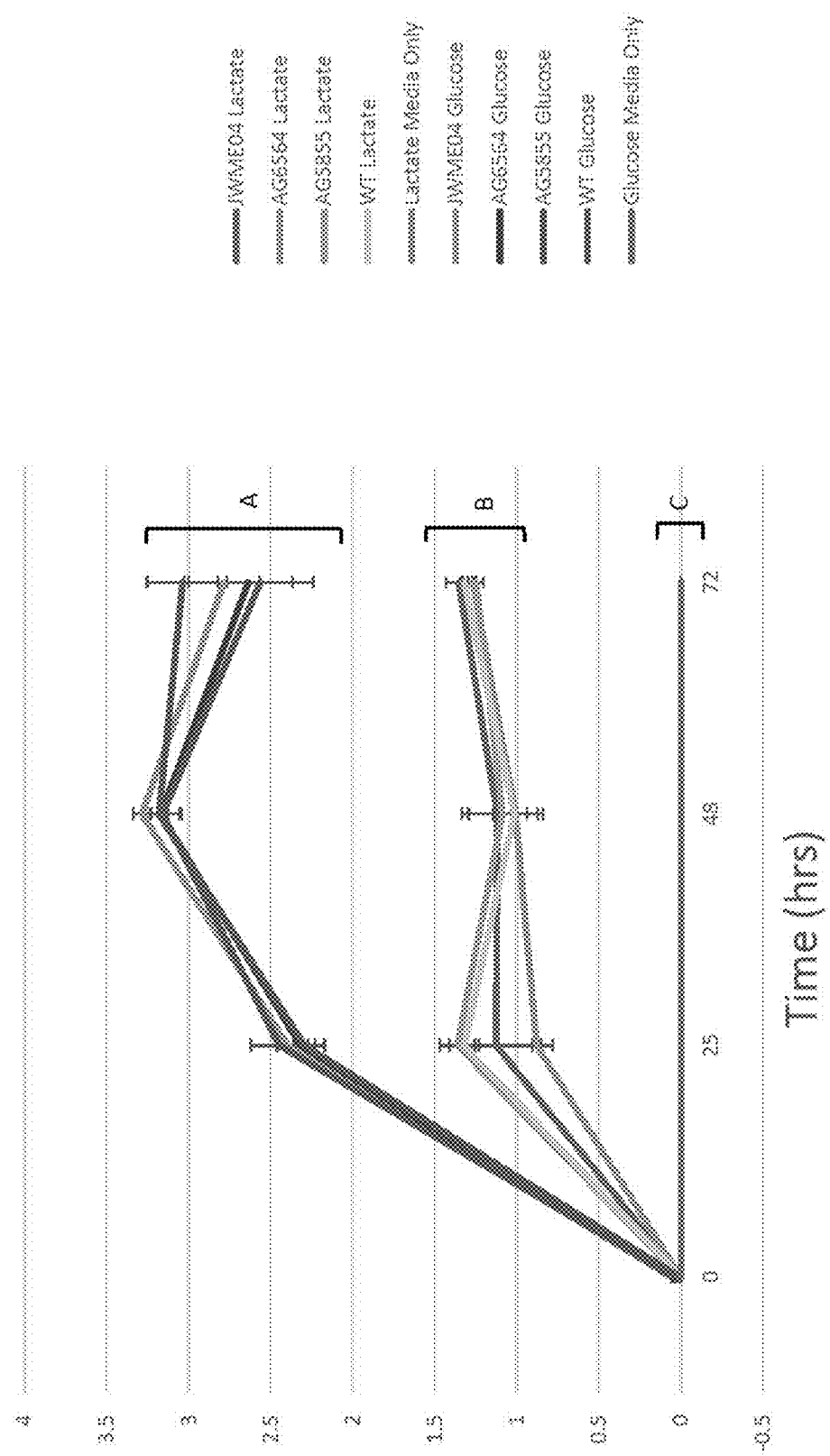
FIG. 5 shows growth of MELS_0742 mutant *M. elsdenii* on lactate and glucose. A; JWME04, AG6564, and AG5855 growth on glucose. B; JWME04, AG6564, AG5855, and wild-type (WT) growth on lactate. C; glucose media only and lactate media only.

There are nine annotated propionate-CoA transferases, (ptc) in *M. elsdenii*. We performed RNAseq and proteomic analysis on wild type *M. elsdenii*, and it revealed that expression of MELS_0742 was highest during growth on lactic acid, and MELS_1130 was not detectable. To investigate the role of the most highly expressed of these, MELS_0742, a deletion of this gene was constructed in the AG5855 (Δupp) background strain, generating strain JWME04. The plasmid designed to generate this deletion contained a cat gene with upstream and downstream homology to MELS_0742 with ΦC31 attachment sites flanking the cat gene. The cat gene allowed selection of marker replacement events and the ΦC31 attachment sites allows subsequent removal of the cat gene for subsequent engineering. Growth of AG5855 (Δupp) and JWME04 (Δupp Δpct::phiC31 attB-cat-ΦC31 attB) was compared to the wild type during growth on both glucose and lactate (FIG. 5). While both strains grew better on glucose, growth of the deletion strains was indistinguishable from wildtype suggesting that these deletions had no effect on growth on either glucose or lactate.

Example 3

Evaluation of Fatty Acid Production and Carbon Substrate Usage

Figure 6A:
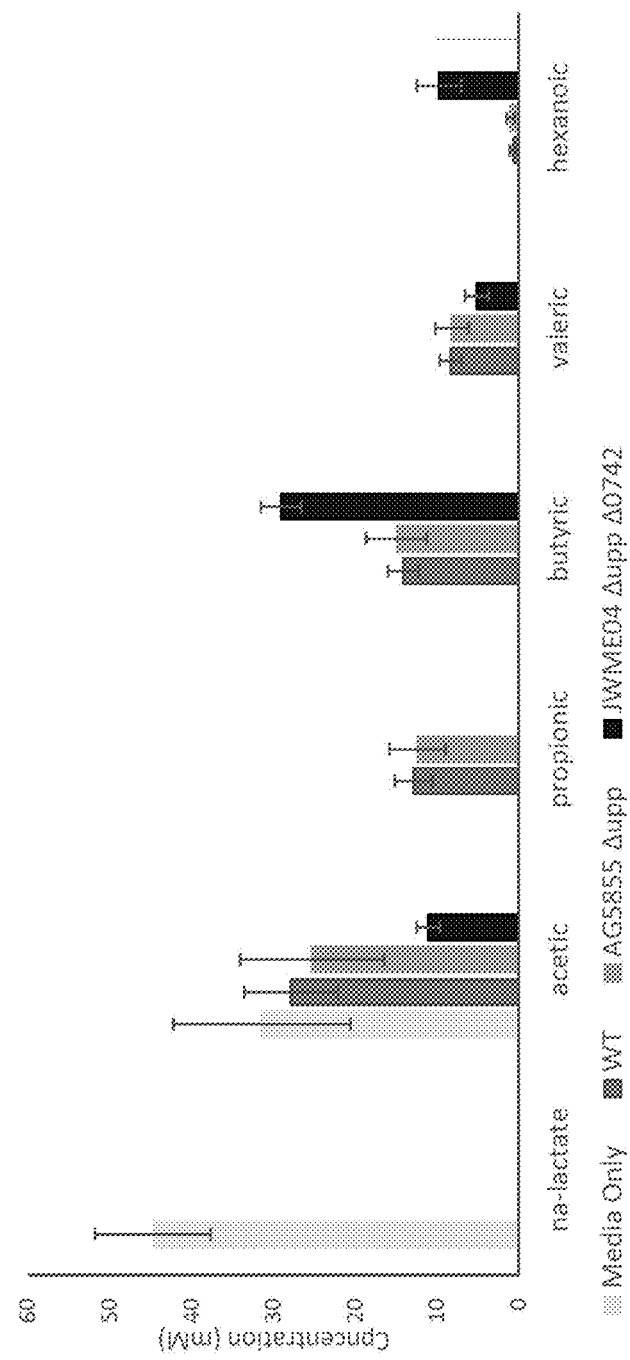
FIGS. 6A and 6B show the effect of the MELS_0742 deletion on fermentation products with lactate or glucose as the growth substrate. Wild type *M. elsdenii* ATCC 25940, *M. elsdenii* ATCC 25940 Δupp (strain AG5855), and *M. elsdenii* ATCC 25940 MELS_0742::ΦC31-cat-ΦC31 (strain JWME04) were grown in (A) 5 mL RCM+5 g/L sodium lactate or (B) 5 mL RCM+5 g/L glucose, with 5 μg/mL thiamphenicol if necessary, overnight. Each strain (50 μL) was added to Balch tubes containing 10 mL of modified RCM with lactate and separately with glucose for 72 hours at 37° C. Lactic, acetic, propionic, butyric, valeric, and hexanoic acids in supernatant following culture were quantified via HPLC. Error bars represent standard deviation from the mean of 5 replicates.
Figure 6B:
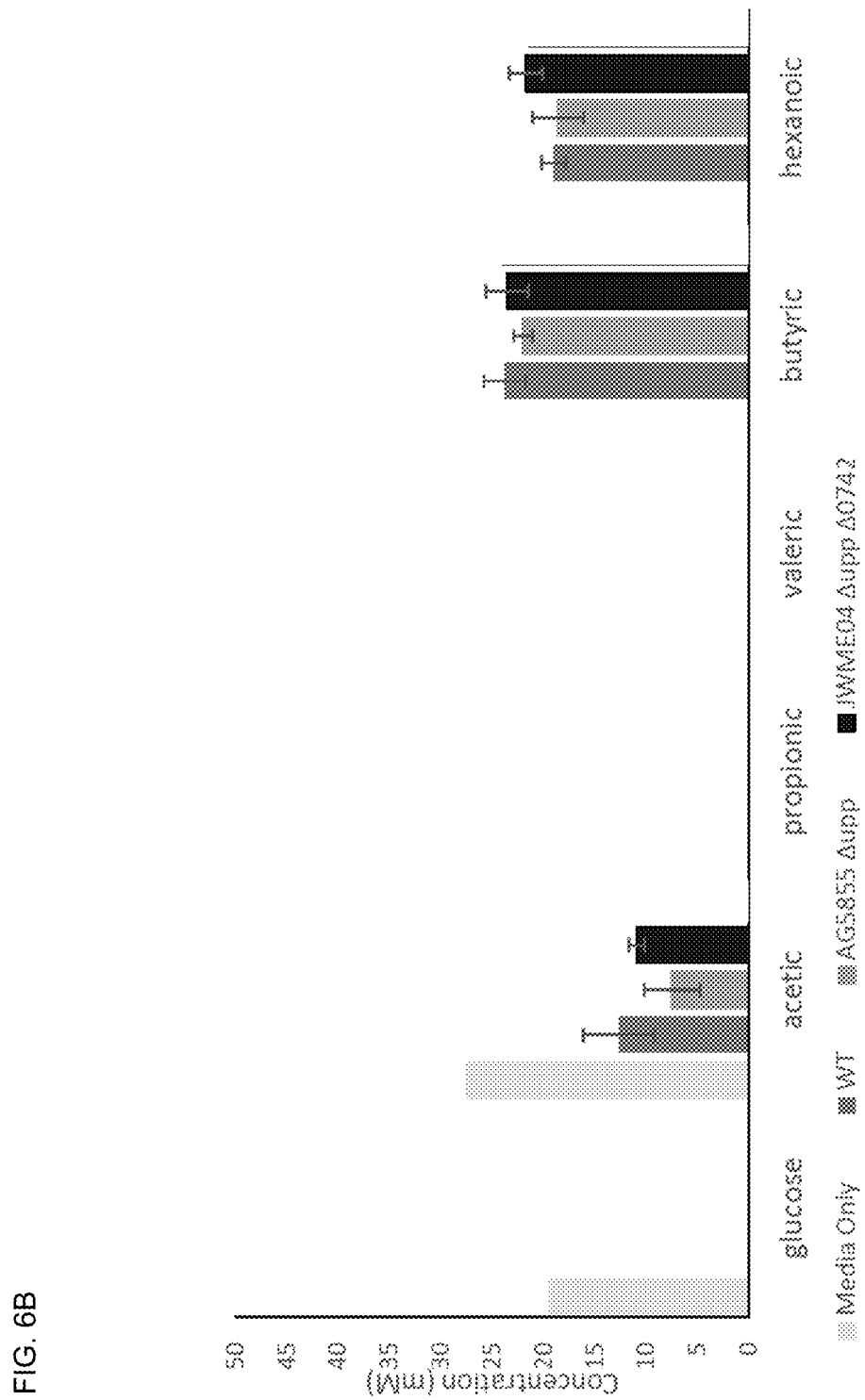

To investigate the effect MELS_0742 on organic acid production, High Performance Liquid Chromatography (HPLC) analysis was performed on cells grown in either glucose or lactate. As shown in FIGS. 6A and 6B, there was a complete loss of propionate production and a significant reduction in valerate production in the strain lacking MELS_0742. *M. elsdenii* ATCC 25940 wild type, *M. elsdenii* ATCC 25940 Δupp (strain AG5855), and *M. elsdenii* ATCC 25940 MELS_0742::ΦC31-cat-ΦC31 (strain JWME04) were grown in 5 mL RCM (HiMedia)+5 µg/mL thiamphenicol, if necessary, overnight. 50 µL of each strain was added to Balch tubes containing 10 mL of modified RCM with lactate and, separately, with glucose. Each strain was cultured in duplicate for 72 hours at 37° C. Samples were taken at 24-hour intervals, optical densities measurements taken, and fermentation products were quantified using HPLC. Lactate, glucose, acetic acid, butyric acid, valeric acid, propionic acid, (and octanoic acid) were quantified on Agilent 1260 infinity series HPLC with the Aminex-HPX-87H column (Bio-Rad). The mobile phase was 5 mM sulfuric acid. The column was heated at 65° C., the flow rate was 0.6 mL/min, and the chromatograph was visualized using an RI detector.

Example 4

Methods Transformation of *M. elsdenii*

Seed cultures of *M. elsdenii* ATCC 25940 were grown, inoculated and grown to stationary phase in 500 mL RCM. Competent cells were prepared at room temperature, and the washes were performed with a 250 mM sucrose, 10% glucose solution. Electrocompetent cells (20 µL) were electroporated with 1 µg of DNA. A 1 mM cuvette was used and electroporated with a square wave at 1200 v and 1.5 ms using a Bio-Rad GenePulser. After electroporation, cells were recovered in 1 mL RCM (BD Difco) and incubated for 3 hours. Cells were then plated in molten RCM+1.5% agar, and, once the agar solidified, they were incubated for 2-3 days at 37° C. in sealed boxes in an anaerobic chamber.

Example 5

Figure 7A:
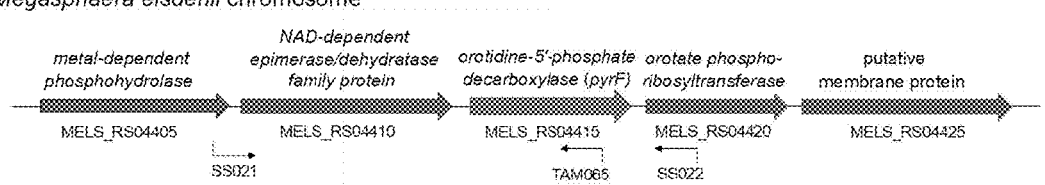
FIGS. 7A and 7B show show schematics depicting the deletion of the CDS encoding an orotidine-5'-phosphate decarboxylase MELS_RS04415.
Figure 7B:
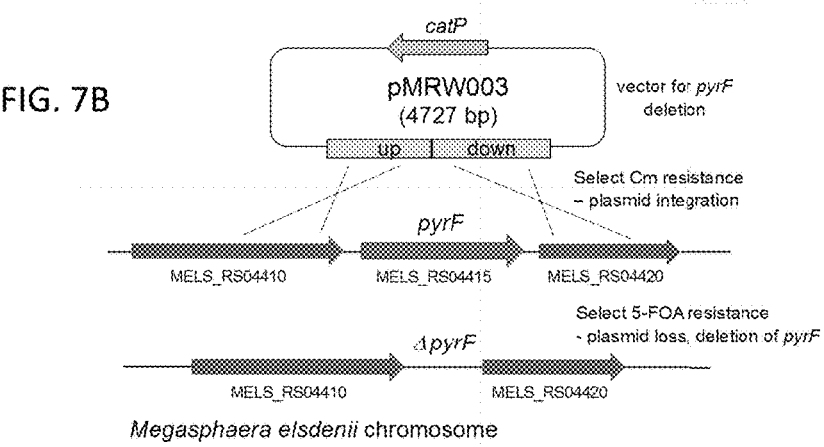

Deletion of pyrF in *Megasphaera elsdenii* Results in Resistance to 5-FOA, Allowing Selection and Counter Selection of Genetic Markers and Facilitates Strain Construction The native ability to condense acetyl-CoA groups to efficiently generate C4 to C8 compounds makes *Megasphaera elsdenii* a compelling platform for the production of fuels and chemicals from lactate and plant carbohydrates. Our overall objective is to develop *M. elsdenii* as a platform for the conversion of lignocellulosic biomass sugars and organic acids into longer chain alcohols such as hexanol as well as other valuable chemicals. While progress has been made in developing basic genetic tools in this strain methods for DNA transformation rely on in vivo methylation of DNA in a strain of *E. coli* that contains two methyltransferases from *M. elsdenii*. A deletion of pyrF that allows counter selection of plasmids containing the wild type allele is constructed as shown in FIG. 7.

Example 6

Defined Medium for *Megasphaera*

A defined medium for any strain of *Megasphaera* was developed. A defined medium allows for mass balance analysis and manipulation of carbon and nitrogen sources to study and manipulate increased production of organic acids. This defined medium is also useful for the selection of uracil prototrophy, making pyrF both a selectable and a counter-selectable marker. The defined medium is produced by combining the following:

TABLE 3

| | Amino Acids | | | |
|---|---|---|---|---|
| Component | Molar Mass (g) | g used/L media | Molarity | Working molarity |
| L-Alanine | 89.09 | 0.0038 | 4.26535E−05 | 43 µM |
| L-Arginine | 174.2 | 0.0062 | 3.55913E−05 | 36 µM |
| L-Asparagine monohydrate | 150.13 | 0.005 | 3.33045E−05 | 33 µM |
| L-Aspartic acid sodium salt monohydrate | 173.1 | 0.0024 | 1.38648E−05 | 14 µM |
| L-Glutamic acid monosodium salt | 169.11 | 0.01 | 5.91331E−05 | 59 µM |
| L-Glutamine | 146.1 | 0.0024 | 1.64271E−05 | 16 µM |
| Glycine | 75.07 | 0.01 | 0.000133209 | 13 µM |
| L-Isoleucine | 131.17 | 0.005 | 3.81185E−05 | 38 µM |
| L-Leucine | 131.17 | 0.005 | 3.81185E−05 | 38 µM |
| L-Lysine HCl | 182.65 | 0.005 | 2.73748E−05 | 27 µM |

TABLE 3-continued

Amino Acids

| Component | Molar Mass (g) | g used/L media | Molarity | Working molarity |
|---|---|---|---|---|
| L-Methionine | 149.21 | 0.0038 | 2.54675E−05 | 25 µM |
| L-Phenylalanine | 165.19 | 0.0019 | 1.15019E−05 | 12 µM |
| L-Proline | 115.13 | 0.0062 | 5.38522E−05 | 54 µM |
| L-Serine | 105.09 | 0.0038 | 3.61595E−05 | 36 µM |
| L-Threonine | 119.12 | 0.005 | 4.19745E−05 | 42 µM |
| L-Tryptophan | 204.23 | 0.0019 | 9.30324E−06 | 9.3 µM |
| Cystein HCl H2O* | 175.63 | 0.018125 | 0.0001032 | 103 µM |

*Added separately as a reducing agent

TABLE 4

No Carbon Buffer

| Component | Molar Mass (g) | g used/L media | Molarity | Working molarity |
|---|---|---|---|---|
| Potassium phosphate monobasic | 136.09 | 2.72 | 0.019986773 | 20 mM |
| Ammonium Sulfate | 132.14 | 2.64 | 0.01997881 | 20 mM |

TABLE 5

Carbon sources

| Component | Molar Mass (g) | g used/L media | Molarity | Working molarity |
|---|---|---|---|---|
| alpha-D(+)Glucose anhydrous contains approx. 5% beta anomer | 180.2 | 5 | 0.027746948 | 28 mM |
| OR | | | | |
| Na-lactate | 112.06 | 4.7 | 0.041941817 | 42 mM |
| OR | | | | |
| Lactic acid | 89.07 | 3.7365 | 0.041950152 | 42 mM |

TABLE 6

Caldi vitamin mix

| Component | Molar Mass (g) | g used/L media | Molarity | Working molarity |
|---|---|---|---|---|
| Biotin | 244.31 | 0.00002 | 8.18632E−08 | 82 nM |
| Folic acid | 441.41 | 0.00002 | 4.53093E−08 | 45 nM |
| Pyridoxine HCl | 205.6 | 0.0001 | 4.86381E−07 | 486 nM |
| Thiamine HCl × 2H$_2$O | 337.3 | 0.00005 | 1.48236E−07 | 148 nM |
| Riboflavin | 376.4 | 0.00005 | 1.32837E−07 | 133 nM |
| Nicotinic acid | 123.1 | 0.00005 | 4.06174E−07 | 406 nM |
| D CaPentothenate | 476.5 | 0.00005 | 1.04932E−07 | 105 nM |
| Vitamin B12 | 1355.37 | 0.000001 | 7.37806E−10 | 0.74 nM |
| p-amino-benzoic acid | 159.1 | 0.00005 | 3.14268E−07 | 314 nM |
| Lipoic acid | 206.32 | 0.00005 | 2.42342E−07 | 242 nM |

TABLE 7

Bacillus trace elements

| Component | Molar Mass (g) | g used/L media | Molarity | Working molarity |
|---|---|---|---|---|
| CaCl$_2$ | 110.98 | 0.000055 | 4.95585E−07 | 496 nM |
| FeCl$_2$ | 126.751 | 0.00014 | 1.10453E−06 | 1.1 µM |
| MnCl$_2$•4H$_2$O | 197.91 | 0.00001 | 5.0528E−08 | 51 nM |
| ZnCl$_2$ | 136.286 | 0.00002 | 1.4675E−07 | 147 nM |
| CuCl$_2$•2H$_2$O | 170.48 | 0.000004 | 2.34632E−08 | 23 nM |
| CoCl$_2$•6H$_2$O | 237.93 | 0.000006 | 2.52175E−08 | 25 nM |
| Na2MoO4 | 205.92 | 0.000006 | 2.91375E−08 | 29 nM |
| Na2SeO4 | 188.94 | 0.0000047 | 2.48756E−08 | 25 nM |
| 1M HCl | | 0.000002 | 0.000002 | 2 µM |

TABLE 8

Magnesium sulfate

| Component | Molar Mass (g) | g used/L media | Molarity | Working molarity |
|---|---|---|---|---|
| Magnesium sulfate | 120.366 | 0.120366 | 0.001 | 1 mM |

TABLE 9

Cysteine

| Component | Molar Mass (g) | g used/L media | Molarity | Working molarity |
|---|---|---|---|---|
| Cysteine HCl | 175.63 | 0.725 | 0.004127996 | 4.1 mM |

TABLE 10

Resazurin

| Component | Molar Mass (g) | g used/L media | Molarity | Working molarity |
|---|---|---|---|---|
| Resazurin | 229.191 | 0.000025 | 1.09079E−07 | 109 nM |

TABLE 11

Sodium acetate

| Component | Molar Mass (g) | g used/L media | Molarity | Working molarity |
|---|---|---|---|---|
| Sodium acetate anhydrous | 82.03 | 2.78 | 0.03389004 | 34 mM |

CITATIONS

Nelson R S, Peterson D J, Karp E M, Beckham G T, Salvachua D. Mixed Carboxylic Acid Production by *Megasphaera elsdenii* from Glucose and Lignocellulosic Hydrolysate. Fermentation. 2017 March; 3(10).

Lamsen E N, Atsumi S. Recent progress in synthetic biology for microbial production of C3-C10 alcohols. Front Microbiol. 2012;3:196. doi: 10.3389/fmicb.2012.00196. eCollection 2012. PubMed PMID: 22701113; PubMed Central PMCID: PMC3370425.

Tracy B P, Jones S W, Fast A G, Indurthi D C, Papoutsakis E T. Clostridia: the importance of their exceptional substrate and metabolite diversity for biofuel and biorefinery applications. Curr Opin Biotechnol. 2012 June; 23(3): 364-81. doi: 10.1016/j.copbio.2011.10.008. Epub 2011 Nov. 11. Review. PubMed PMID: 22079352.

Weimer P J, Nerdahl M, Brandl D J. Production of medium-chain volatile fatty acids by mixed ruminal microorganisms is enhanced by ethanol in co-culture with *Clostridium kluyveri*. Bioresour Technol. 2015 January; 175:97-101. doi: 10.1016/j.biortech.2014.10.054. Epub 2014 Oct. 18. PubMed PMID: 25459809.

Dekishima Y, Lan E I, Shen C R, Cho K M, Liao J C. Extending carbon chain length of 1-butanol pathway for 1-hexanol synthesis from glucose by engineered *Escherichia coli*. J Am Chem Soc. 2011 Aug. 3; 133(30):11399-401. doi: 10.1021/ja203814d. Epub 2011 Jul. 7. PubMed PMID: 21707101.

Clomburg J M, Vick J E, Blankschien M D, Rodriguez-Moya M, Gonzalez R: A synthetic biology approach to engineer a functional reversal of the beta-oxidation cycle. ACS Synth Biol 2012, 1(11):541-554.

Kim S, Clomburg J M, Gonzalez R. Synthesis of medium-chain length (C6-C10) fuels and chemicals via β-oxidation reversal in *Escherichia coli*. J Ind Microbiol Biotechnol. 2015 March; 42(3):465-75. doi: 10.1007/s10295-015-1589-6. Epub 2015 Feb. 3. PubMed PMID: 25645093.

Kataoka N, Vangnai A S, Pongtharangkul T, Yakushi T, Matsushita K: Butyrate production under aerobic growth conditions by engineered *Escherichia coli*. Journal of bioscience and bioengineering 2017, 123(5):562-568.

Dellomonaco C, Clomburg J M, Miller E N, Gonzalez R: Engineered reversal of the beta-oxidation cycle for the synthesis of fuels and chemicals. Nature 2011, 476(7360): 355-359.

Zhang X, Mao Y, Wang B, Cui Z, Zhang Z, Wang Z, Chen T. Screening, expression, purification and characterization of CoA-transferases for lactoyl-CoA generation. J Ind Microbiol Biotechnol. 2019 Jul. 1; 46(7):899-909.

Prabhu R, Altman E, Eiteman M A. Lactate and acrylate metabolism by *Megasphaera elsdenii* under batch and steady-state conditions. Appl Environ Microbiol. 2012 December; 78(24):8564-70. doi: 10.1128/AEM.02443-12. Epub 2012 Sep. 28. PubMed PMID: 23023753; PubMed Central PMCID: PMC3502912.

Singh V, Brecik M, Mukherjee R, Evans J C, Svetlíková Z, Blaško J, Surade S, Blackburn J, Warner D F, Mikušová K, Mizrahi V. The complex mechanism of antimycobacterial action of 5-fluorouracil. Chem Biol. 2015 Jan. 22; 22(1):63-75. doi: 10.1016/j.chembiol.2014.11.006. Epub 2014 Dec. 24. PMID: 25544046.

Projan S J, Monod M, Narayanan C S, Dubnau D. Replication properties of pIM13, a naturally occurring plasmid found in *Bacillus subtilis*, and of its close relative pE5, a plasmid native to *Staphylococcus aureus*. J Bacteriol. 1987; 169(11):5131-5139. doi:10.1128/jb.169.11.5131-5139.1987

De Rossi E, Milano A, Brigidi P, Bini F, Riccardi G. Structural organization of pBC1, a cryptic plasmid from *Bacillus coagulans*. J Bacteriol. 1992; 174(2):638-642. doi:10.1128/jb.174.2.638-642.1992

Liu J, Xie Z, Merritt J, Qi F. Establishment of a tractable genetic transformation system in *Veillonella* spp. Appl Environ Microbiol. 2012 May; 78(9):3488-91. doi: 10.1128/AEM.00196-12. Epub 2012 Feb. 17. PMID: 22344660; PMCID: PMC3346448.

Hatmaker et al., 2019, Complete genome sequences of two *Megasphaera elsdenii* strains, NCIMB 702410 and ATCC 25940. Microbiol Resour Announc, 8:e01430-18. doi.org/10.1128/MRA.01430-18.

Guss and Riley, US Published Patent Application No. 2021/0024965.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The invention claimed is:

1. A recombinant *Megasphaera* microbe genetically modified to (i) consume a greater amount of acetate than a comparable control microbe, or (ii) produce a greater amount of butyrate, hexanoate, or a combination thereof, than a comparable control microbe, or (iii) increase carbon flux to butyryl-CoA and/or hexanoyl-CoA than a comparable control microbe, or a combination thereof, wherein the recombinant *Megasphaera* microbe comprises a mutation of a CoA-transferase coding region, a mutation of a glyoxalase coding region, or a mutation of a lyase coding region, and the comparable control microbe is a microbe genetically identical to the recombinant *Megasphaera* microbe except for the mutation of the CoA-transferase coding region, the glyoxalase coding region, or the lyase coding region.

2. The recombinant *Megasphaera* microbe of claim 1, wherein the recombinant *Megasphaera* microbe is *M. elsdenii*.

3. The recombinant *Megasphaera* microbe of claim 2, wherein the *M. elsdenii* is a modified ATCC 25940.

4. The recombinant *Megasphaera* microbe of claim 1, wherein the mutation of the CoA-transferase coding region comprises a deletion of the CoA-transferase coding region.

5. The recombinant *Megasphaera* microbe of claim 1, wherein the CoA-transferase coding region encodes a propionyl-CoA transferase.

6. The recombinant *Megasphaera* microbe of claim 5, wherein propionate production by the recombinant *Megasphaera* microbe is undetectable.

7. The recombinant *Megasphaera* microbe of claim 1, wherein the CoA-transferase coding region is MELS_0742 (SEQ ID NO: 22), MELS_0464 (SEQ ID NO: 23), MELS_1631 (SEQ ID NO: 24), or MELS_1130 (SEQ ID NO: 25), or a combination thereof.

8. The recombinant *Megasphaera* microbe of claim 7, wherein the recombinant *Megasphaera* microbe comprises a mutation of at least 1, CoA-transferase coding regions selected from MELS_0742 (SEQ ID NO: 22), MELS_0464 (SEQ ID NO: 23), and MELS_0034 (SEQ ID NO: 26), or mutation of all 3 CoA-transferase coding regions.

9. The recombinant *Megasphaera* microbe of claim 1, wherein the mutation of the glyoxalase coding region comprises a deletion of the glyoxalase coding region.

10. The recombinant *Megasphaera* microbe of claim 9, wherein the glyoxalase coding region is MELS_0743 (SEQ ID NO: 27).

11. The recombinant *Megasphaera* microbe of claim 1, wherein the mutation of the lyase coding region comprises a deletion of the lyase coding region.

12. The recombinant *Megasphaera* microbe of claim 11, wherein the lyase coding region is MELS_0745 (SEQ ID NO: 28).

13. The recombinant *Megasphaera* microbe of claim 1, wherein the amount of butyrate or hexanoate produced is at least 2-fold greater than the comparable control microbe.

14. The recombinant *Megasphaera* microbe of claim 1, wherein the consumption of acetate is at least 2-fold greater than the comparable control microbe.

15. A recombinant *Megasphaera* microbe comprising a mutation of a pyrF coding region to result in undetectable expression of the pyrF coding region (SEQ ID NO: 29).

16. The recombinant *Megasphaera* microbe of claim 15, wherein the mutation is a deletion of the pyrF coding region.

17. The recombinant *Megasphaera* microbe of claim 15, wherein the *Megasphaera* microbe is *M. elsdenii*.

18. The recombinant *Megasphaera* microbe of claim 17, wherein the *M. elsdenii* is a modified ATCC 25940.

19. The recombinant *Megasphaera* microbe of claim 15, wherein the pyrF coding region is MELS_RS04415 (SEQ ID NO: 2).

20. A method for increasing carbon flux to acetoacetyl-CoA, comprising:
incubating the recombinant *Megasphaera* microbe of claim 1 with lactate as a carbon source under conditions suitable for replication, wherein the carbon flux to acetoacetyl-CoA in the recombinant *Megasphaera* is at a level greater than the comparable control microbe.

21. A method for producing butyrate, hexanoate, or combination thereof, comprising:
incubating the recombinant *Megasphaera* microbe of claim 1 with lactate as a carbon source under conditions suitable for replication, wherein the recombinant *Megasphaera* produces butyrate, hexanoate, or combination thereof at a level greater than the a comparable control microbe.

22. A method for genetically engineering a *Megasphaera*, comprising:
providing the recombinant *Megasphaera* of claim 15,
transforming the recombinant *Megasphaera* with a plasmid comprising a pyrF coding region and a mutagenic cassette,
wherein the mutagenic cassette of the plasmid comprises a marker flanked by DNA sequences,
wherein the DNA sequences are selected to result in homologous recombination between the plasmid and two regions of DNA present in the recombinant *Megasphaera* that flank a coding region targeted for mutation; and
incubating the transformed recombinant *Megasphaera* under conditions suitable for positive selection of the transformed recombinant *Megasphaera* and counter selection of the transformed recombinant *Megasphaera* to select for those that have lost the pyrF coding region,
wherein the transformed recombinant *Megasphaera* identified by the positive and counter selection comprise a mutation of the coding region targeted for mutation.

23. The method of claim 22, wherein the mutagenic cassette of the plasmid further comprises attachment sites flanking the marker, wherein the attachment sites are between the marker and the DNA sequences, and wherein the attachment sites are identified by a recombinase that can promote recombination between the two attachment sites and deletion of the marker flanked by the attachment sites.

24. The method of claim 22, wherein the mutation of the coding region targeted for mutation comprises a deletion of the targeted coding region.

* * * * *